United States Patent [19]

Webster, Jr.

[11] Patent Number: 4,717,653
[45] Date of Patent: Jan. 5, 1988

[54] METHOD FOR IDENTIFYING AND CHARACTERIZING ORGANISMS

[76] Inventor: John A. Webster, Jr., 8343 Carrleigh Pkwy., Springfield, Va. 22152

[21] Appl. No.: 305,498

[22] Filed: Sep. 25, 1981

[51] Int. Cl.$^4$ ............... C12Q 1/70; C12Q 1/68; C12Q 1/16; C12N 15/00
[52] U.S. Cl. ............... 435/5; 435/6; 435/35; 435/39; 435/172.3; 435/803; 436/501; 935/78
[58] Field of Search ............... 435/5, 6, 29, 34, 35, 435/91, 39, 172, 4, 803, 810, 172.3; 436/504, 543, 545, 81, 73, 804, 94, 801; 536/27, 28; 424/1, 1.5; 935/78

[56] References Cited

U.S. PATENT DOCUMENTS

| | | | |
|---|---|---|---|
| 4,283,489 | 8/1981 | Goodman et al. | 435/6 |
| 4,302,204 | 11/1981 | Wahl et al. | 435/6 |
| 4,358,535 | 11/1982 | Falkow et al. | 435/5 |
| 4,396,713 | 8/1983 | Simpson et al. | 435/34 |
| 4,526,865 | 7/1985 | Silman | 435/35 |

OTHER PUBLICATIONS

Fox et al., International Journal of Systematic Bacteriology, 27(1), 44–57 (1977).
Woese et al., Nucleic Acids Research, 8(10): 2275–2293, (1980).
Atchison et al., Molec. Gen. Genet., 148, 263–269, (1969).
MacKay et al., Nucleic Acids Res., 9, 3321–3328, (1981).
Fox et al., Science, 209, 457–463, (1980).
Edwards et al., Nucleic Acids Res., 9, 2853–2869, (1981).
Van Etten et al., Cell, 22, 157–170, (Nov. 1980).
Delseny et al., Biochem. Biophys. Res. Commun., 91, 540–547, (1979).
Rochaix et al., Cell, 15, 661–670, (1978).
Whitfield, Nucleic Acids Res. 5, 1741–1751, (1978).
Bedbrook et al., PNAS U.S.A., 73(12), 4309–4313, (1976).
Bonen et al., Nucleic Acids Res., 8, 319–335, (1980).
Tompkins et al., J. Infect. Dis., 141, 625–636, (1980).
Beljanski et al., C.R. Akad. Sci. Paris, t286, 1825–1828, (1978).
Taylor et al., Biochim. Biophys. Acta, 442, 324–330, (1976).
Arnheim et al., PNAS U.S.A. 77(12), 7323–7327, (Dec. 1980).
Krystal et al., PNAS U.S.A., 78(9), 5744–5748, (Sep. 1981).
Krystal et al., J. Mol. Biol., 126, 91–104, (1978).
Arnheim et al., Cell, 11, 363–370, (1977).
Schmickel et al., Am. J. Hum. Genet., 32, 890–897, (1980).
Proc. Nat. Acad. Sci. U.S.A., vol. 71, No. 4, pp. 1035–1039, Apr. 1974, Gulati et al., "Conditions for Using DNA Polymerase I as an RNA-Dependent DNA Polymerase".
Biochemical and Biophysical Research Communications, vol. 59, No. 1, 1974, pp. 202–214, Sarin et al., "Transcription of Heteropolymeric Regions of Avian Myeloblastosis Virus High Molecular Weight RNA with Escherichia coli DNA Polymerase I".

(List continued on next page.)

Primary Examiner—Esther M. Kepplinger
Attorney, Agent, or Firm—Saidman, Sterne, Kessler & Goldstein

[57] ABSTRACT

A method of characterizing an unknown organism which comprises comparing the chromatographic pattern of restriction endonuclease-digester DNA from the unknown organism, which digested DNA has been hybridized or reassociated with ribosomal RNA information-containing nucleic acid from or derived from a known probe organizm, with at least two equivalent chromatographic patterns, each one of the equivalent chromatographic patterns defining a known different organism species; and establishing the species of the unknown organism by means of a conserved set of ribosomal RNA sequence-containing restriction fragments present in the chromatographic pattern of the unknown organism.

41 Claims, 16 Drawing Figures

OTHER PUBLICATIONS

*Proc. Nat. Acad. Sci. U.S.A.*, vol. 71, No. 5, pp. 1585–1589, May 1974, Beljanski et al., "Isolation of the Tumor-Inducing RNA from Oncogenic and Nononcogenic *Agrobacterium tumefaciens*".

*C. R. Acad. Sc. Paris*, t. 288 (Jan. 8, 1979), pp. 147–150, Le Goff et al., "Biologie Moleculaire".

*Molecular Biology Reports* 2, (1976), 497–506, Beljanski et al., "Particular Small Size RNA and RNA Fragments from Different Origins as Tumor Inducing Agents in *Datura stramonium*".

*Bergey's Manual of Systematic Bacteriology*, vol. 1, 1974, pp. 279–288.

Brochure: "API 20A, Anaerobe Identification in Only 24 Hours."

*International Code of Nomenclature of Bacteria and [Selected]Statutes . . . Bacteriological Code*, 1976 Revision; ASM, Washington, D.C. 1975.

*International Journal of Systematic Bacteriology*, vol. 30, No. 1, Jan. 1980, pp. 106–122, DeSmedt et al., "Intra— and Intergeneric Similarities of Ribosomal Ribonucleic Acid Cistrons of Free-Living, Nitrogen-Fixing Bacteria".

*International Journal of Systematic Bacteriology*, vol. 30, No. 1, Jan. 1980, pp. 7–27, Gillis et al., "Intra— and Intergeneric Similarities of the Ribosomal Ribonucleic Acid Cistrons of Acetobacter and Gluconobacter".

*International Journal of Systematic Bacteriology*, vol. 27, No. 3, Jul. 1977, pp. 222–240, DeSmedt et al., "Intra— and Intergeneric Similarities of Agrobacterium Ribosomal Ribonucleic Acid Cistrons".

*Mol Gen. Genet*, 182:502–504 (1981), Sawada et al., "The Number of Ribosomal RNA Genes in *Mycoplasma capricolum*".

Lamppa, Mol. Gen. Genet. 182: 310–320, (1981).

Ostapchuk et al., ibid, 180: 475–477, (1980).

Potter et al., Proceedings of the National Academy of Sciences U.S.A., 72: 4496–4500, (1975).

Brenner, D. J., *International Journal of Systematic Bacteriology* 23:4, pp. 298–307.

Modarski, M. et al., *Jour. of Gen'l Microbiol.*, 118:313–319, (1980).

Doi, R. H. et al., *J. of Bacteriol.*, vol. 92, No. 1, pp. 88–96, (Jul. 1966).

Bohnert, H. J. et al., *Molec. Gen. Genet* 179:539–545, (1980).

Moore, R. L. et al., *J. Bacteriol.*, vol. 94, No. 4, pp. 1066–1074, (Oct. 1967).

Sinclair, J. H. et al., *Biochemistry*, 10:2761, (1971).

Woese, Carl R., "Archaebacteria".

PST I digested DNA from P. aeruginosa strains

FIG. 3 EcoR I digested DNA from Pseudomonas and Acinetobacter species

FIG. 4 PST I digested DNA from Pseudomonas and Acinetobacter species

FIG. 5 EcoR I digested DNA from Bacillus subtilis strains

FIG. 7  Bgl II digested DNA from Bacillus subtilis strains

Sac I digested DNA from Bacillus subtilis strains

EcoR I digested DNA from B. subtilis RH 3021 and B. polymyxa RH 3074, RH 3033, RH 3062, RH 3073

PST I digested DNA from B. subtilis RH 3021 and B. polymyxa RH 3074, RH 3033, RH 3062, RH 3073

FIG. 11  Bgl II and Sac I digested DNA from
B. subtilis RH 3021 and B. polymyxa RH 3074

FIG. 12  Detection of S. pneumoniae RH 3077 ribosomal gene sequences in EcoR I digested DNA from infected mouse tissues

METHOD FOR IDENTIFYING AND CHARACTERIZING ORGANISMS

BACKGROUND OF THE INVENTION

1. Field of the Invention

The present invention relates to a method for the rapid and accurate characterization and identification of organisms, including prokaryotic and eukaryotic organisms, such as bacteria, plants, and animals.

2. Description of the Prior Art

The classification of living organisms has traditionally been done along more or less arbitrary and somewhat artificial lines. For example, the living world has been divided into two kingdoms: Plantae (plants) and Animalia (animals). This classification works well for generally familiar organisms, but becomes difficult for such organisms as unicellular ones (e.g., green flagellates, bacteria, blue-green algae), since these differ in fundamental ways from the "plants" and "animals".

It has been suggested to simply divide organisms with respect to the internal architecture of the cell. In this scheme, all cellular organisms are either prokaryotic or eukaryotic. Prokaryotes are less complex than eukaryotes, they lack internal compartmentalization by unit membrane systems, and lack a defined nucleus. Prokaryotic genetic information is carried in the cytoplasm on double-stranded, circular DNA; no other DNA is present in cells (except for the possible presence of phage, bacterial viruses, and circular DNA plasmids, capable of autonomous replication). Eukaryotes on the other hand have a multiplicity of unit membrane systems which serve to segregate many of the functional components into specialized and isolated regions. For example, genetic information (DNA) can be found in a well-compartmentalized nucleus and also in organelles: mitochondria and (in photosynthetic organisms) chloroplasts. The replication, transcription, and translation of the eukaryotic genome occurs at either two or three distinct sites within the cell: in the nucleocytoplasmic region, in the mitochondrion and in the chloroplast.

The differences between prokaryotes and eukaryotes, however, breaks down when a comparison of mitochondria and chloroplasts is carried out with prokaryotes: these organelles are today considered to have been derived from free-living prokaryotes, which entered into an endosymbiotic relation with primitive eukaryotes, and eventually became closely integrated with the machinery of the host cell and incapable of independent existence (see e.g., Fox, G.E., et al, Science 209:457–463 (1980), at 462; Stanier, R. Y. et al, "The Microbial World", Fourth Edition, Prentice-Hall, Inc. 1976, at p. 86). For example, it has been demonstrated that DNA from mouse L cell mitochondria carrying the ribosomal RNA gene region exhibits notable sequence homologies to *Escherichia coli* ribosomal RNA, thus providing strong support for the endosymbiotic model (Van Etten, R. A., et al, Cell, 22:157–170 (1980)). It has also been shown that the nucleotide sequence of 23S ribosomal DNA from *Zea mays* chloroplast has 71% homology with 23S ribosomal DNA from *E. coli* (Edwards, K. and Kossel, H., Nucleic Acids Research, 9:2853–2869 (1981)); other related work (Bonen, L. and Gray, M. W., ibid, 8:319–335 (1980)) also further supports the general concept.

In this model the eukaryotic cell is a phylogenetic "chimera" with organelle components that are clearly prokaryotic in nature. The "prokaryoticeukcaryotic" dichotomy then, also has drawbacks, even as a broad classification method.

Where classification of organisms becomes more than a scientific exercise is in the identification of plants and animals for hybridization and breeding purposes, and in the accurate and reliable identification of microorganisms which may infect so-called "higher" organisms or other media. For example, the plant-breeder, cattle breeder, or fish breeder may wish to have a quick and reliable means of identifying different species and strains of their subjects. The veterinarian, physician, or horticulturist may wish to have an accurate identification of any infectious organisms (parasites, fungi, bacteria, etc.) and viruses present in examined plant or animal tissues. The correct identification of species of these organisms and viruses is of particular importance.

The problem can best be illustrated by referring to the identification of bacteria. Names of bacterial species usually represent many strains, and a strain is considered to be a population derived from a single cell. Strains of a species have similar sets of attributes which serve to define the species. Precise definitions of bacterial species are difficult to express because subjective limits to strain diversity within species are required to define species boundaries. (Buchanan, R. E., International Bulletin of Bacteriological Nomenclature and Taxonomy, 15:25–32 (1965)). The practical application of definitions of species to the identification of an unknown bacterial strain requires the selection of relevant probes, such as substrates and conditions to detect phenotypic attributes, and radioactively-labeled DNA from the same species. It is necessary to use a screening procedure to presumptively identify the strain so that the appropriate probe can be selected to identify the strain. The challenge is to precisely define the boundaries of species, preferably in terms of a standard probe which reveals species-specific information, so that definitions of species can be directly and equally applied to the identification of unknown strains.

Bergey's Manual of Determinative Bacteriology (Buchanan, R. E. and Gibbons, N. E., Editors, 1974, 8th Edition, The Williams & Wilkins Company, Baltimore) provides the most comprehensive treatment of bacterial classification particularly for nomenclature, type strains, pertinent literature, and the like. It is, however, only a starting point for the identification of any species since, inter alia, it is normally out of date, and is limited in space to describing species quite briefly. (See for example Brenner, D. J. "Manual of Clinical Microbiology", 3rd Edition, American Society of Microbiology, Washington, D.C. 1980, pages 1–6).

The term "species", as applied to bacteria, has been defined as a distinct kind of organism, having certain distinguishing features, and as a group of organisms which generally bear a close resemblance to one another in the more essential features of their organization. The problem with these definitions is that they are subjective; Brenner, supra, at page 2. Species have also been defined solely on the basis of criteria such as host range, pathogenicity, ability or inability to produce gas in the fermentation of a given sugar, and rapid or delayed fermentation of sugars.

In the 1960's, numerical bacterial taxonomy (also called computer or phenetic taxonomy) became widely used. Numerical taxonomy is based on an examination of as much of the organism's genetic potential as possible. By classifying on the basis of a large number of characteristics, it is possible to form groups of strains with a stated degree of similarity and consider them species. Tests which are valuable for the characterization of one species, however, may not be useful for the next, so this means to define species is not directly and practically applicable to the identification of unknown strains. Although this may be overcome in part by selecting attributes which seem to be species specific, when these attributes are used to identify unknown strains, the species definition is applied indirectly. See for example Brenner, supra at pages 2-6. The general method, furthermore, suffers from several problems when it is used as the sole basis for defining a species, among them the number and nature of the tests to be used, whether the tests should be weighted and how, what level of similarity should be chosen to reflect relatedness, whether the same level of similarities is applicable to all groups, etc.

Hugh R. H. and Giliardi, G. L. "Manual of Clinical Microbiology", 2nd Edition, American Society for Microbiology, Washington, D.C., 1974, pages 250-269, list minimal phenotypic characters as a means to define bacterial species that makes use of fractions of genomes. By studying a large, randomly selected sample of strains of a species, the attributes most highly conserved or common to a vast majority of the strains can be selected to define the species. The use of minimal characters is progressive and begins with a screening procedure to presumptively identify a strain, so that the appropriate additional media can be selected. Then the known conserved attributes of the species are studied with the expectation that the strain will have most of the minimal characters. Some of the minimal characters do not occur in all strains of the species. A related concept is the comparative study of the type, the neo-type, or a recognized reference strain of the species. This control is necessary because media and procedures may differ among laboratories, and it is the strain, not the procedure, that is the standard for the species.

A molecular approach to bacterial classification is to compare two genomes by DNA-DNA reassociation. A genetic definition of species includes the provision that strains of species are 70% or more related. With DNA-DNA reassociation a strain can be identified only if the radioactively labeled DNA probe and unknown DNA are from the same species. The practical application of this 70% species definition however is limited by selection of an appropriate probe. This may be overcome in part by selecting phenotypic attributes which seem to correlate with the reassociation group, but when these are used alone the DNA-DNA reassociation species definition is also applied indirectly.

Brenner, supra at page 3, states that
the ideal means of identifying bacterial species would be a 'black box' which would separate genes, and instantly compare the nucleic acid sequences in a given strain with a standard pattern for every known species—something akin to mass spectrophotometric analysis.

Brenner, however, concedes that although restriction endonuclease analysis can be done to determine common sequences in isolated genes, "we are not at all close to having an appropriate black box, especially one suited for clinical laboratory use". His words could be equally applied to any species of organisms.

This brief review of the prior art leads to the conclusion that there presently exists a need for a rapid, accurate, and reliable means for identifying unknown bacteria and other organisms, and to quickly classify the same, especially to identify the organism of a disease, or of a desirable biochemical reaction. The method should be generally and readily useful in clinical laboratories, should not be dependent on the number of tests done, on the subjective prejudices of the clinician, nor the fortuitous or unfortuitous trial and error methods of the past. Further, a need also exists for a method useful for identifying and distinguishing genera and species of *any* living organism, which can be readily and reliably used by veterinarians, plant-breeders, toxicologists, animal breeders, entomologists and in other related areas, where such identification is necessary.

SUMMARY OF THE INVENTION

It is therefore an object of the invention to provide a quick, reliable and accurate method of objectively identifying organisms, especially—but not limited to—microorganisms.

Yet another object of the invention is to provide a method of identifying organisms such as bacteria which utilizes the organisms' genome.

Another object of the invention is to provide a method of characterizing and identifying species and genera of pathogenic organisms in the clinical laboratory, so as to provide the capability of characterizing and identifying the cause of any given animal or plant disease.

Still another object of the invention is to provide various products useful in the aforementioned methodologies.

These and other objects of the invention, as will hereinafter become more readily apparent, have been attained by providing:

A method of characterizing an organism which comprises comparing the chromatographic pattern of restriction endonuclease-digested DNA from said organism, which digested DNA has been hybridized or reassociated with ribosomal RNA information-containing nucleic acid from or derived from a probe organism, with equivalent chromatographic patterns of at least two different known organisms.

Still another object of the invention has been attained by providing:

A method of diagnosing a pathogenic organism infection in a sample which comprises identifying the organism in said sample by the aforementioned method.

DESCRIPTION OF THE PREFERRED EMBODIMENTS

Figure 1:
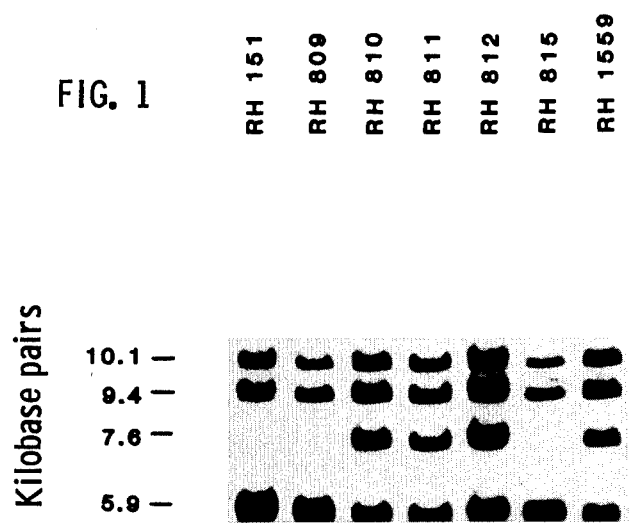
FIG. 1 shows the EcoR I restriction endonuclease digest of DNA isolated from strains of *Pseudomonas aeruginosa*, using cDNA to 16S and 23S ribosomal RNA (rRNA) of *E. coli* as the probe.

This invention is based on the inventor's realization that, if species are discrete clusters of strains related to a common speciation event, there should be, despite divergence, a likeness shared by strains that objectively defines the species boundary; strains of species should contain structural information which is a clue to their common origin. Since the greatest amount of an organism's past history survives in semantides, DNA and RNA,(Zuckerkandl, E. and Pauling, L., Journal of Theoretical Biology 8:357-366 (1965)), the inventor concluded that an experimental approach which makes use of information contained in a few conserved genes is the use of rRNA. Ribosomal RNA has a structural and functional role in protein synthesis (Schaup, Journal of Theoretical Biology, 70:215-224 (1978)), and the general conclusion from rRNA-DNA hybridization studies, is that the base sequences of ribosomal RNA genes are less likely to change, or are more conserved during evolution, than are the majority of other genes (Moore, R. L. Current Topics In Microbiology and Immunobiology, Vol. 64:105-128 (1974), Springer-Verlag, New York). For example, the primary structure of 16S rRNA from a number of bacterial species has been inferred from oligonucleotide analysis (Fox, G. E., et al, International Journal of Systematic Bacteriology, 27:44-57 (1977)). There are negligble differences in the 16S oligomer catalogs of several strains of *E.coli* (Uchida, T. et al, Journal of Molecular Evolution, 3:63-77 (1974)); the substantial differences among species, however, can be used for a scheme of bacterial phylogeny (Fox, G. E., Science, 209:457-463 (1980)). Different strains of a bacterial species are not necessarily identical; restriction enzyme maps show that different EcoR I sites occur in rRNA genes in two strains of *E. coli* (Boros, I.A. et al, Nucleic Acids Research 6:1817-1830 (1979)). Bacteria appear to share conserved rRNA gene sequences and the other sequences are variable (Fox, 1977, supra).

The present inventor further discovered that restriction endonuclease digests of DNA have sets of fragments containing rRNA gene sequences that are similar in strains of a species of organism (e.g., bacteria), but different in strains of other species of the organism i.e., despite strain variation, enzyme specific sets of restriction fragments containing ribosomal RNA gene sequences, define the species. This is the essence of the invention. The present inventor also discovered that the method is general, in that it is applicable to both eukaryotic and prokaryotic DNA, using a ribosomal nucleic acid probe from any organism, prokaryotic or eukaryotic, of the same or different (classic) taxonomic classification than the organism being identified.

The present invention offers an objective method of defining organisms based on detecting DNA fragments containing ribosomal RNA gene sequences in restriction endonuclease digests. The detection is carried out by hybridizing or reassociating DNA fragments with nucleic acid containing rRNA information from a probe organism.

By the "organism" which can be characterized (which term is meant to include "identified") by the process of the invention, it is meant to include virtually any organism which, by definition, contains DNA. In this respect it is useful to refer to a classical taxonomic scheme as a point of reference.

All organisms belonging to the Kingdoms Monera, Plantae and Animalia are included. For example, among those of the Kingdom Monera can be mentioned the Schizomycetes (Bacteria) of the classes myxobacteria, spirochetes, eubacteria, rickettsiae, and the cyanopytha (blue green algae). Among those of the Kingdom Plantae can be mentioned the Division Euglenophyta (Euglenoids), Division Chlorophyta (green-algae) classes chlorophyceae and charophyceae; Division Chrysophyta, classes xanthophyceae, chrysophyseae, bacillariophyceae; Division Pyrrophyta (Dinoflagellates); Division Phaeophyta (Brown algae); Division Rhodophyta (Red algae); Division Myxomycophyta (slime molds), classes myxomycetes, acrasiae, plasmodiophoreae, labyrinthuleae; Division Eumycophyta (true fungi), classes phycomycetes, ascomycetes, and basidomycetes; Division Bryophyta, classes hepaticae, anthocerotae, and musci; Division Tracheophyta (Vascular plants), subdivisions psilopsida, lycopsyda, sphenopsida, pteropsida, spermopsida classes cycadae, ginkgoae, coniferae, gneteae and angiospermae subclasses dicotyledoneae, monocotyledoneae. Among those of the Kingdom Animalia can be mentioned the Subkingdom Protozoa, Phylum Protozoa (Acellular animals) subphylum plasmodroma, classes flagellata, sarcodina and sporozoa; subphylum ciliophora, class ciliata; the Subkingdom Parazoa, Phylum porifera (Sponges), classes calcarea, hexactinellida, and desmospongiae; the Subkingdom Mesozoa, phylum mesozoa; the Subkingdom Metazoa, Section Radiata, Phylum coelenterata, classes hydrozoa, scyphozoa, anthozoa, Phylum ctenophora, classes tentaculata and nuda; Section Protostomia Phylum platyhelmintes (flatworms) classes turbellana, trematoda, and cestoda; Phylum nemertina; Phylum acanthocephala; phylum aschelmintles, classes rotifera, gastrotricha, kinorhyncha, priapulida, nematoda and nematomorpha; Phylum entoprocta; Phylum ectoprocta, classes gymnolaemata and phylactolaemata; Phylum phoronida; Phylum brachiopoda, classes inarticulata and articulata; Phylum mollusca (molluscs) classes amphineura, monoplacophora, gastropoda, scaphopoda, pelecypoda, and cephalopoda; Phylum sipunculida; Phylum echiurida; phylum annelida, classes polychaeta, oligochaeta and hirudinea; Phylum onychophora; Phylum tardigrada; phylum pentastomida; phylum arthropoda, subphylum trylobita, subphylum chelicerata classes xiphosura, arachmida, pycnogomida, subphylum mandibulata classes crustacea, chilopoda, diplopoda, pauropoda, symphyla, insecta of the orders collembola, protura, diplura, thysanura, ephemerida, odonata, orthoptera, dermaptera, embiania, plecoptera, zoraptera, corrodentia, mallophaga, anoplura, thysanoptera, hemiptera, neuroptera, coleoptera, hymenoptera, mecoptera, siphonaptera, diptera, trichoptera and lepidoptera; those of the Section Deuterostomia, phylum chaetognatha, phylum echinodermata, classes crinoidea, asterordea, ophiuroidea, echinoidea, and holoturoidea, phylum pogonophora; phylum hemichordata, classes enteropneusta, and pterobranchia; phylum chordata, subphylum urochordata, classes ascidiaciae, thaliaceae, larvacea; subphylum cephalochordata, subphylum vertebrata, classes agnatha, chondrichthyes, osteichthyes (subclass saccopteiygii orders crossopterygii and dipnoi), amphibia, reptilia, aves and mammalia, subclass prototheria, subclass theria, orders marsupialia, insectivora, dermoptera, chiroptera, primates, edentata, pholidota, lagomorpha, rodentia, cetaceae, carnivora, tubulidentata, probosicdea, hyracoidea, sirenia, perissodactyla and artiodactyla. It is understood that beyond the order, the organisms are still classified according to their families, tribes, genus and species, and even subspecies, infrasubspecific taxons, and strains or individuals. In addition cell cultures (plant or animal), as well as viruses can also be identified. These classifications are used in this application for illustrative purposes only, and are not to be taken as exclusive. The organism is either known or unknown, most commonly the organism is an unknown being identified.

Functionally, for the purposes of this invention, it is convenient to divide all organisms into the eukaryotes and the prokaryotes. When identifying a prokaryotic organism, the DNA to be endonuclease-digested is that present in the cells or in the non-compartmentalized chromosomes. When identifying a eukaryotic organism one may either use the nuclear DNA or the organelle DNA (mitochondrial DNA or chloroplast DNA), and endonuclease-digest the same.

Briefly, high molecular weight DNA and/or small circular DNAs are isolated from the organism to be identified in order to analyze the rRNA gene sequences and possibly sequences that could be used to create a taxon below the rank of species or infrasubspecific subdivisions. The DNA's are extracted by methods which are well known to the art. The DNA's are cut at specific sites into fragments, by restriction endonucleases. The fragments are separated according to size by a standard chromatographic system, such as gel electrophoresis. The gels are stained, as is otherwise well known in the art, and standardized as to the fragment sizes using standard curves constructed with fragments of known sizes. The separated fragments are then transferred to nitrocellulose paper by the Southern blot technique (Southern, E.M., Journal of Molecular Biology, 38:503–517 (1975), herein incorporated by reference), and covalently bound thereto by heating. The fragments containing the rRNA gene sequences are then located, by their capacity to hybridize with a nucleic acid probe containing rRNA information. The nucleic acid probe can either be nonradioactively labeled or (preferably) radioactively labeled. When radioactively labeled, the probe can be ribosomal RNA (rRNA), or radioactively labeled DNA which is complementary to ribosomal RNA (rRNAcDNA), either synthesized by reverse transcription or contained on a cloned fragment, which can be labeled, for example, by nick translation.

The probe is derived from an arbitrarily chosen organism, see infra. Once hybridization has occurred, the hybridized fragments are detected by selectively detecting double stranded nucleic acid (non-radiolabeled probe), or visualized by, e.g. autoradiography (radiolabeled probe). The size of each fragment which has been hybridized is determined from the distance traveled using standard curves as described previously. The amount of hybridization, the pattern of hybridization, and the size of the hybridized fragments can be used individually or in conjunction to identify the organism.

The pattern that emerges from this hybridization can be readily compared to equivalent chromatographic patterns derived from at least two and up to a multiplicity of known, standard organisms, genera or species. After a preliminary broad classification has already been carried out (using, for example, classical taxonomy), the comparison can be either by visual inspection and matching of appropriate chromatographic patterns, by comparison of nucleic acid fragment sizes, by band intensity (amount of hybridization) or by any combination thereof. Ideally, the comparison is carried out with a one-dimensional computer-based pattern recognition system, such as those used in point-of-sale transactions.

The present inventor discovered that when using the aforementioned method, the chromatographic patterns for organisms of the same species are substantially similar, with minor variations allowed for intraspecies differences due to strain variations, whereas differences between species, and differences between genera (and higher classifications) are maximal.

The use of enzyme-specific fragment variations in strains of a species even permits the typing of strains for various purposes; e.g. in the case of bacteria, for epidemiological purposes. In fact, restriction enzymes can be chosen for their ability to distinguish strains within species.

The "probe organism" used in the present invention, and from which is obtained the nucleic acid probe, can also be any of the aforementioned organisms; it can be either eukaryotic or prokaryotic. The only limitation is given by the fact that the rRNA-containing probe should hybridize maximally with the endonuclease digest of the unknown organism's DNA.

There are four types of ribosomal RNA information-containing probes: (1) prokaryotic ribosomal probe (especially bacterial-derived rRNA), (2) eukaryotic mitochondrial ribosomal probe, (3) eukaryotic chloroplast ribosomal probe, and (4) eukaryotic non-organelle ribosomal probe. There are also four sources of DNA (to be endonuclease digested): (1) prokaryotic cellular DNA, (2) eukaryotic mitochondrial DNA, (3) eukaryotic chloroplast DNA, and (4) eukaryotic nuclear DNA. The following hybridization Table can thus be constructed (Table 1).

TABLE 1
Hybridization Table

| Unknown organism DNA | Ribosomal Probe | | | |
|---|---|---|---|---|
| | Prokaryotic | Eukaryotic | | |
| | | Mitochondrial | Chloroplast | Non-organelle |
| Prokaryotic | + | + | + | − |
| Eu.[1] Mitochondria | + | + | + | − |
| Eu. Chloroplast | + | + | + | − |
| Eu. Nuclear | −[2] | − | − | + |

[1] Eu = Eukaryotic
[2] = refers to less effective hybridization, see Example 4, infra.

The Table shows which ribosomal RNA probes can be maximally hybridized with which unknown DNA. For example, one can identify a eukaryotic organism by extracting species specific mitochondrial or chloroplast DNA, endonuclease-digesting it and hybridizing the digest with either a prokaryotic ribosomal RNA probe, or with an organelle derived eukaryotic ribosomal probe. In the same manner, one can identify a prokaryotic organism by extracting species-specific cellular DNA, endonuclease-digesting it, and hybridizing the digest with either a prokaryotic ribosomal RNA probe, or an organelle-derived eukaryotic ribosomal RNA probe. Also, one can identify a eukaryotic organism by extracting and digesting species-specific nuclear DNA, and hybridizing it with a nonorganelle derived eukaryotic ribosomal probe. Eukaryotes could be defined by one or any combination of the nuclear, mitochondria, or in some cases chloroplast systems. These cross-hybridizations are based on the previously mentioned fact that rRNA nucleic acid derived from eukaryotic organelles has extensive homology with prokaryotic rRNA nucleic acid, but that the same homologies are not present to such extent between nuclear-derived eukaryotic DNA and prokaryotic DNA.

In essence, because the genetic code is universal, because all cells (eukaryotic or prokaryotic) require ribosomes to translate the information of the code into protein, and because ribosomal RNA is highly conserved, there are sufficient homologies between the cross-hybridizing elements ("+" on Table 1) to assure that the method will work as indicated.

The choice of any pair of DNA to be digested and accompanying ribosomal probe is arbitrary, and will depend on the organism being identified, i.e. it will depend on the question asked. For example, in detecting a prokaryotic species (e.g. bacteria) present in a eukaryotic cell (e.g. animal or plant) for purposes of detecting and identifying an infecting agent, one may choose a prokaryotic ribosomal probe and work under conditions where organelle-derived DNA is not extracted or, only minimally extracted. In this manner one assures that interference between organelle-derived DNA and prokaryotic DNA is minimal. In identifying a eukaryotic species (which is not infected with a prokaryote) with a prokaryotic ribosomal probe, it is best to maximize the concentration of organelle-derived DNA, as for example by separating organelles from nuclei, and then extracting only organelle DNA. If one wishes to identify a eukaryotic organism which has been infected with a prokaryotic organism, it is best to use a non-organelle, non-prokaryotic derived ribosomal probe since it will not hybridize well with the DNA from the prokaryote.

It is preferred to use a pair (DNA and ribosomal probe) from the same kingdom, or same subkingdom, or same section, or same phylum, or same subphylum, or same class, or same subclass, or same order, or same family or same tribe or same genus. It is particularly preferred to use prokaryotic ribosomal probe (e.g. bacterial ribosomal probe) to hybridize with prokaryotic DNA. In this manner one could detect, quantify, and identify genera, species, and strains of prokaryotic organisms. One of the most preferred prokaryotic ribosomal probes is derived from bacteria and further, because of the ease and availability, from *E. coli*. The ribosomal probe from *E. coli* can be used to identify any organism, especially any prokaryotic organism, most preferably any bacterial genera, species or strains. Another particularly preferred embodiment is to use eukaryotic ribosomal probe derived from a given class to identify eukaryotic organisms of the same class (e.g. mammalian ribosomal probe to identify mammalian organisms). Most preferred is to use ribosomal probe and DNA from the same subclass and/or order and/or family of organisms, (e.g. if identifying a species of mouse, it is preferred to use mouse-derived ribosomal probe).

The most sensitive and useful pair systems are those where there is less evolutionary distance or diversity between the source of the ribosomal probe and restricted DNA.

The individual steps involved in the technique are generally known in the art. They will be described hereinafter broadly with reference to both eukaryotic and prokaryotic cells when applicable, or specifically for each type of cell if some difference in technique exists.

The first step is extraction of the DNA from the unknown organism. Nuclear DNA from eukaryotic cells can be selectively extracted by standard methodology well known to the art (see for example Drohan, W. et al, Biochem. Biophys. Acta 521 (1978) 1–15, herein incorporated by reference). Because organelle DNA is small and circular, spooling techniques serve to separate the non-circular nuclear DNA from the circular, organelle-derived DNA. As a corollary, the non-spooled material contains the organelle-derived DNA which can separately be isolated by density gradient centrifugation. Alternatively mitochondria (or chloroplasts) are separated from a mixture of disrupted cells; the purified mitochondrial (or chloroplast) fraction is used for the preparation of organelle-derived DNA while the purified nuclear fraction is used to prepare nuclear DNA. (see for example Bonen L. and Gray, M. W., Nucleic Acids Research 8:319–335 (1980)).

Prokaryotic DNA extraction is also well known in the art. Thus, for example, an unknown bacterium present in any medium, such as an industrial fermentation suspension, agar medium, plant or animal tissue or sample or the like, is treated under well known conditions designed to extract high molecular weight DNA therefrom. For example, cells of the unknown organism can be suspended in extraction buffer, lysozyme added thereto, and the suspension incubated. Cell disruption can be further accelerated by addition of detergents, and/or by increase in temperature. Protease digestion followed by chloroform/ phenol extraction and ethanol precipitation can be used to finalize the extraction of DNA. An alternative method of extraction, which is much faster than phenol/chloroform extraction, is rapid isolation of DNA using ethanol precipitaton. This method is preferably used to isolate DNA directly from colonies or small, liquid cultures. The method is described in Davis, R. W. et al: "A Manual for Genetic Engineering, Advanced Bacterial Genetics", (hereinafter "Davis") Cold Spring Harbor Laboratory, Cold Spring, Harbor, N.Y., 1980, pp. 120-121, herein incorporated by reference.

The DNA (prokaryotic or eukaryotic (nuclear or nonnuclear)) is dissolved in physiological buffer for the next step.

Digestion of extracted DNA is carried out with restriction endonuclease enzymes. Any restriction endonuclease enzyme can be used, provided of course that it is not from the same organism species as that being identified, since otherwise, the DNA may remain intact. (This may, in any event, identify the organism, since the enzymes are not expected to cut DNA from the species of their origin). Since the organism species being characterized may be unknown, obtaining a digest of fragments may entail a minimum amount of trial and error, which can routinely be carried out by those skilled in the art without undue experimentation. Examples of possible restriction endonuclease enzymes are Bgl I, BamH I, EcoR I, Pst I, Hind III, Bal I, Hga I, Sal I, Xba I, Sac I, Sst I, Bcl I, Xho I, Kpn I, Pvu II, Sau IIIa, or the like. See also Davis, supra, at pp 228-230, herein incorporated by reference. A mixture of one or more endonucleases can also be used for the digestion. Normally, DNA and endonuclease are incubated together in an appropriate buffer for an appropriate period of time (ranging from 1 to 48 hours, at temperatures ranging from 25° C.-65° C., preferably 37° C.).

The resulting chromatographic pattern will depend on the type or types of endonucleases utilized, and will be endonuclease-specific. It is therefore necessary to note which enzyme or enzymes have been used for the digestion since the comparative patterns used in the catalog should have been prepared using the same enzyme or enzymes.

After endonuclease digestion, the incubation mixture, which contains fragments of varying sizes, is separated thereinto by an appropriate chromatographic method. Any method which is capable of separating nucleic acid digests according to size, and which allows the eventual hybridization with the nucleic acid probe, can be used. Preferred is gel electrophoresis, most preferred is agarose gel electrophoresis. In this system, the DNA digests are normally electrophoresed in an appropriate buffer, the gels are normally immersed in an ethidium bromide solution, and placed on a UV-light box to visualize standard marker fragments which may have been added.

After separation and visualization, the DNA fragments are transferred onto nitrocellulose filter paper by the method of Southern (Journal of Molecular Biology, 38:503-517 (1975)). The transfer can be carried out after denaturation and neutralization steps, and is usually done for long periods of time (approximately 10-20 hours) or, alternatively by means of an electrically driven transfer from gel to paper. Instruments used to accelerate the transfer from gel to paper are commercially available. The receiving nitrocellulose filter papers are then normally baked at high temperatures (60°-80° C.) for several hours, to bind the DNA to the filter.

The probe utilized for the hybridization of the paper-bound DNA digest fragments is a nucleic acid probe preferably from a given well-defined organism. It may be detectably labeled or non-labeled, preferably detectably labeled. In such case, it is either detectably labeled ribosomal RNA (rRNA) from such organism, nick-translated labeled DNA probes containing ribosomal information, cloned DNA probes containing ribosomal information, or detectably labeled DNA which is complementary to the ribosomal RNA from the probe organism (rRNAcDNA). Depending on the choice of pair, the ribosomal probe may be from a prokaryote, or from a eukaryote (cytoplasm-derived, or organelle derived). Most preferably, the detectable label is a radioactive label such as radioactive phosphorus (e.g., $^{32}$p, $^3$H or $^{14}$C). The isolation of rRNA from eukaryotes or prokaryotes is well known in the art. For example, to prepare rRNA from eukaryotic cytoplasmic ribosomes, RNA can be extracted from whole cells or ribosomes, separated by sucrose gradient centrifugation, and the 18S and 28S fractions can be collected using known molecular weight markers. (See for example Perry, R. P. and D. E. Kelley, "Persistent Synthesis of 5S RNA when Production of 28S and 18S Ribosomal RNA is Inhibited by Low Doses of Actinomycin D", J. Cell. Physiol. 72:235-246 (1968), herein incorporated by reference). As a corollary, organelle-derived rRNA is isolated and purified from the organelle fractions in the same manner (see e.g. Van Etten, R. A., et al, Cell 22:157-170 (1980), or Edwards, K. et al, Nucleic Acids Research 9:2853-2869 (1981)).

If radioactively labeled ribosomal RNA probe is used, the same is isolated from the probe organism after growth or cultivation of the organism with nutrients or in culture media containing appropriately radioactive compounds. When the probe is complementary DNA (rRNAcDNA), the same is prepared by reverse transcribing isolated rRNA from the probe organism, in the presence of radioactive nucleoside triphosphates (e.g., $^{32}$p-nucleosides or $^3$H-nucleosides).

The labeled ribosomal probe may also be a nick-translated DNA molecule, especially one obtained from organelle-derived whole circular DNA. In this embodiment, chloroplast or mitochondrial circular DNA is nick-translated in the presence of radiolabel, and a labeled DNA ribosomal probe is thereby obtained. The chloroplast labeled probe will hybridize best with chloroplast DNA, and the mitochondrial labeled probe will hybridize best with mitochondrial DNA. The chloroplast (or mitochondrial) nick-translated labeled ribosomal probe will hybridize second best with mitochondrial (or chloroplast) DNA; it will also hybridize, albeit in less favorable fashion, with whole plasnt (or animal) DNA. The ribosomal probe may also be obtained from eukaryotic nuclear DNA by nick-translation, although practical considerations would rule against this mode. A more useful approach in this embodiment is to cut out rRNA genes from the nuclear eukaryotic DNA (by restriction enzymes), separate the fragments, identify the ribosomal gene sequences (as by hybridization), and isolate the ribosomal gene sequences (as by electrophoresis). The isolated rRNA sequences may then be recombined into a plasmid or vector, and after transformation of an appropriate host, cloned in $^{32}$p-containing media. Alternatively, the transformed host is grown, and the DNA is then isolated and labeled by nick-translation; or the DNA is isolated, the rRNA sequence are cut out and then labeled. The resulting ribosomal probe will hybridize in the same instances as rRNAcDNA (see infra).

The preferred nucleic acid probe is radioactively labeled DNA complementary to rRNA from the probe organism. In this embodiment, rRNA is purified from the probe organism by isolating the ribosomes and separating and substantially purifying therefrom the appropriate RNA as described supra. The ribosomal RNA is thus ribosome-free and is also substantially free of other RNA's such as transfer RNA (tRNA) or messenger RNA (mRNA). Prokaryotic rRNA normally contains three subspecies: the so-called 5S, 16S and 23S fragments. The reverse transcription into cDNA can be carried out with a mixture of all three, or alternatively, with a mixture of 16S and 23S fragments. It is less preferred to carry out the reverse transcription with only one of the components, although under certain conditions this may be feasible. Eukaryotic rRNA normally contains two subspecies: 18S and 28S, and the reverse transcription into cDNA can be carried out with a mixture of 18S and 28S fragments or with each.

The pure rRNA, substantially free of other types of RNA, is incubated with any reverse transcriptase capable of reverse transcribing it into cDNA, preferably with reverse transcriptase from avian myeloblastosis virus (AMV) in the presence of a primer such as calf thymus DNA hydrolysate. The mixture should contain appropriate deoxynucleoside triphosphates, wherein at least one of said nucleosides is radioactively labeled, for example with $^{32}P$. For example, deoxycytidine 5'-($^{32}P$), deoxythymidine 5'-($^{32}P$), deoxyadenine 5'-($^{32}P$), or deoxyguanidine 5'-($^{32}P$) triphosphates can be used as the radioactive nucleosides. After incubation, from 30 minutes to 5 hours at 25° C.–40° C., extraction with chloroform and phenol, and centrifugation as well as chromatography, the radioactively labeled fractions are pooled, and constitute the cDNA probe. The radioactively labeled cDNA probe in substantially purified form, i.e., free of non-labeled molecules, free of cDNA which is complementary to other types of RNA, free of proteinaceous materials as well as free of cellular components such as membranes, organelles and the like, also constitutes an aspect of the present invention. A preferred probe is prokaryotic labelled rRNAcDNA, most preferred being the bacterial labelled rRNAcDNA. The probe species can be any bacterial microorganism, such as those of the family Enterobacteriaceae, Brucella, Bacillus, Pseudomonas, Lactobacillus, Haemophilus, Micobacterium, Vibrio, Neisseria, Bactroides and other anaerobic groups, Legionella, and the like. Although the prokaryotic examples in the present application are limited to the use of *E. coli* as a bacterial prokaryotic probe organism, this aspect of the invention is by no means limited to this microorganism. The use of cDNA in radioactively labeled form as the probe is preferred to the use of radioactively labeled ribosomal RNA because DNA has greater stability during hybridization.

It is important to recognize that the labeled cDNA probe should be a faithful copy of the rRNA, i.e. be one wherein all nucleotide sequences of the template rRNA are transcribed each time the synthesis is carried out. The use of a primer is essential in this respect. That the cDNA is a faithful copy can be demonstrated by the fact that it should have two properties following hybridization:

1. The cDNA should protect 100% of labeled rRNA from ribonuclease digestion; and
2. The labeled cDNA should specifically anneal to the rRNA as shown by resistance to S1 nuclease.

Beljanski M. M. et al, C.R. Acad. Sc Paris t 286, Serie D. p. 1825–1828 (1978), describe $^3H$ radioactively labeled cDNA derived from *E.coli* rRNA. The cDNA in this work was not prepared with reverse transcriptase in the presence of a primer as in the present invention, but was prepared with a DNA polymerase I, using as a template rRNA which had been pre-cleaved using ribonuclease $U_2$. The rRNA digestion product (with RNAse $U_2$) of Beljanski et al has a different base ratio than the initial rRNA, indicating a loss of bases and/or loss of short fragments. Thus the cDNA obtained therefrom is not a faithful copy. In addition, the use of DNA polymerase I used by Beljanski is known to favor predominance of homopolymeric over heteropolymeric transcription of rRNA (see Sarin, P.S., et al, Biochem. Biophys. Res. Comm., 59:202–214 (1974)).

In sum, the "ribosomal" probe can be seen as being derived (a) from genome DNA containing rRNA genes, by cloning and/or nick-translation, (b) from ribosomal RNA itself or (c) from rRNAcDNA by reverse transcription of rRNA.

The next step in the process of the invention is the hybridization of the separated DNA digest from the unknown organism with the unlabeled or (preferably) radioactively labeled rRNA or cDNA probe. Hybridization is carried out by contacting the paper containing covalently labeled DNA digest from the unknown, with a hybridization mix containing the ribosomal probe. Incubation is carried out at elevated temperatures (50°–70° C.) for long periods of time, filter papers are then washed to remove unbound radioactivity (if needed), air dried and readied for detection. An alternative, highly preferred hybridization, which is much more rapid than the one described above, is the room temperature phenol emulsion reassociation technique of Kohne, D. E. et al, Biochemistry, 16:5329–5341 (1977), which is herein incorporated by reference.

After hybridization, the technique requires selective detection of the appropriately hybridized fragments. This detection can be carried out by taking advantage of the double strandedness of the hybridized fragments and using a selective method therefor (for nonlabeled probe), or by autoradiography or by an appropriate radiation scanner which may or may not be computerized, and which may increase the speed of detection (for labeled probe). These techniques are well known to those skilled in the art and will not be further described at this point.

The end product of the technique is a chromatographic band pattern having light and dark regions of various intensities at specific locations. These locations can be readily matched to specific fragment sizes (in kilobase pairs) by introduction into the separation technique of a marker, such as EcoR I digested λ bacteriophage DNA. In this manner, both the relative position of the bands to each other, as well as the absolute size of each band can be readily ascertained. The band pattern for the unknown is then compared with band patterns present in a catalog or library. The catalog or library can consist of a book containing patterns for at least two, and up to a virtually unlimited number of defined different organisms genera and species. For example, the number of pathologically relevant bacteria that cause human disease is estimated to be about 100, so it is estimated that a standard catalog of pathogenic bacteria would contain anywhere between 50 and 150 such patterns. A catalog of types of bacterial strains for epidemiological typing systems can also be included.

The band patterns will depend on the type or types of endonuclease enzymes used, possibly on the particular organism used as the source for the radioactively labeled probe (the probe organism), and on the composition of the ribosomal RNA information utilized to prepare the probe (e.g. containing either prokaryotic 5S, 16S or 23S subtypes, or only 16S and 23S, or the like). Thus, the catalog may, for each probe, contain a variety of enzyme-specific band patterns, with the size of each band listed, and with the relative intensity noted. As the concentration of the bound DNA bound to the filter decreases, only the most intense bands can be seen, and the size of this band or bands can thus identify species. Each one of these band patterns may in turn comprise a band pattern obtained for complete ribosomal RNA and/or a band pattern obtained for ribosomal RNA containing only certain subtypes. Any variation or permutation of the above can of course be used for the library. Additionally, for a eukaryotic organism the library may contain patterns that result from the use of one type of DNA or any combination of organelle and/or nuclear DNA. The pattern for each DNA digest will depend on the probe composition. The catalog may be arranged so that if more than one strain or species is present in the extracted sample and detected by the probe, the resulting pattern can be interpreted.

A user can either compare the obtained band pattern visually, or by aid of a one-dimensional, computer assisted, digital scanner programmed for recognition of patterns. These computer scanners are well known in the art of the time-of-sale transactions (the commonly utilized "supermarket" check-out pattern readers). Ideally, the library or catalog is present in a computer memory both in terms of the relative band patterns for a plurality of organisms, and in terms of the absolute values of molecular weight or size of the fragments. The catalog comparison then consists of matching the unknown pattern with one of the patterns present in the library by means of either one or both of the stored information elements (relative patterns and/or absolute size elements). The intensity of each band when compared to a standard can also reveal the amount of bound DNA hybridized, and thus can be used to estimate the extent of the presence of a an organism, for example a prokaryote in a eukaryote.

If a user wishes to further confirm the nature and identification of a given organism, such user can digest the unknown with a second, different endonuclease, and compare the resulting band pattern to catalog band patterns of the organism for the second chosen endonuclease. This process can be repeated as many times as necessary to get an accurate identification. Normally, however, a single analysis with a single probe would be sufficient in most instances.

The present invention and its variations can be used for a myriad of applications. It may be used by plant or animal breeders to correctly identify their subjects, or it may be used by clinical and microbiological laboratories to identify bacteria, parasites or fungi present in any medium, including in eukaryotic cells. In this latter use, the method is preferred to the standard microbiological assays, since it does not require isolation and growth of the microbes. In vitro growth and characterization is now either impossible for some microorganisms such as *Mycobacterium leprae* (agent of leprosy), impossible on standard media for some microorganisms such as the obligate intracellular bacteria (e.g. rickettsia, chlamydia, etc), or highly dangerous (e.g. *B. anthracis* (agent of anthrax)). The present method depends on the isolation of nucleic acid and avoids these problems since it avoids conventional bacterial isolation and characterization.

The method is expected to detect microorganisms that have not yet been conventionally described. In addition, the present method allows distinguishing different strains of species, and this can be useful, for example, for epidemiological typing in bacteriology. The method can be used by forensic laboratories to correctly and unambiguously identify plant or animal tissues in criminal investigations. It can also be used by entomologists to quickly identify insect species, when ascertaining the nature of crop infestations.

In addition, upon the conjunction of the method with the identification of infrasubspecific taxons (such as e.g., nitrogenase genes in plant roots, see Hennecke, H. 291 Nature 354 (1981)), the methodology can be utilized to search for and identify the genotypes of individual strains.

The method of this invention is preferably used for the identification of microorganisms wherever they may be found. These microorganisms may be found in physiological as well as non-physiological materials. They may be found in industrial growth media, culture broths, or the like, and may be concentrated for example by centrifugation. Preferably, the microorganisms are found in physiological media, most preferably they are found in animal sources infected therewith. In this latter embodiment, the method is used to diagnose bacterial infections in animals, most preferably in humans. The detection and identification of bacterial DNA with a prokaryotic ribosomal probe is highly selective and occurs without hindrance, even in the presence of animal, (e.g., mammalian) DNA. If a prokaryotic ribosomal probe is used, conditions can be selected which minimize hybridization with mitochondrial DNA, or mitochondrial bands can be subtracted from the pattern. The technique can thus be used in clinical laboratories, bacterial depositories, industrial fermentation laboratories, and the like.

Of particular interest is the possibility of detecting, in addition to the species and strain identity of the infecting microorganism, the presence, in the microorganism of any specific genetic sequences. For example, it is possible to detect the presence of antibiotic resistance sequences found on R factors, transmissible plasmids mediating drug resistance. One can add labeled R-factor DNA or cloned labeled antibiotic resistance sequences to the hybridization mixture in order to correctly determine the antibiotic resistance of the organism, (an extra band or bands would appear), or one can rehybridize the once hybridized filter in the presence of added antibiotic resistance sequence probe or probes. Alternatively one could separate the unknown DNA into aliquots, and test the first aliquot for identification, the second for the presence of drug resistance sequences, the third for toxin genes, etc. Alternatively, one could use ribosomal probe labeled with one radionuclide (e.g. $^{32}P$) in a hybridization mixture with added R-factor probe labeled with a different radionuclide (e.g. $^3H$ or $^{14}C$). After hybridization, the presence of R-factor DNA in the unknown DNA can be tested by scanning with two different scanners: One for species and strain identification (e.g. $^{32}P$), the other for drug resistance, or the like (e.g. $^3H$ or $^{14}C$). In this manner the lab can, without isolating and characterizing the microorganism, identify the genus and species, type the strain and test for drug resistance, possible toxin production or any other character or taxon below the rank of species that can be detected with a labeled nucleic acid sequence or probe, all in one experiment.

The R-factors are universal and cross species boundaries, so that identification can be carried out in any bacterial genus or species with the same R-factor probe (see Tomkins, L.S., et al, J. Inf. Dis., 141:625–636 (1981)).

In addition, the presence of viruses or virus-related sequences in eukaryotes or prokaryotes can also be detected and identified in conjunction with the method of the invention: Any of the viruses described in "Manual of Clinical Microbiology", 3d edition, edited by Lennette, E. H., Amer. Soc. Microb., 1980, 774–778 can be identified, eq. picornaviridae, caliciviridae, reoviridae, togaviridae, orthomyxoviridae, paramyxoviridae, rhabdoviridae, retroviridae, arenaviridae, coronaviridae, bunyaviridae, parvoviridae, papovaviridae, adenoviridae, herpesviridae, vidoviridae and poxviridae. (1) When the viral genome is integrated into host DNA (as with DNA viruses, for example members of Papovaviridae, and RNA viruses, for example, members of Retroviridae), high molecular weight DNA is extracted from the tissue and digested with restriction endonucleases. The overall procedure is the same as used for bacteria. The choice of a viral probe again depends on the question asked, and on the extent of homology between the "probe virus" and the viral related sequences to be detected. In order to have suitable sequence homology, it may be necessary that the probe and tissue sequences are related to the same family, genus, or species of virus. In addition to the extent of conserved sequences, whether or not a viral probe hybridizes to viral related sequences in host DNA may be determined by the hybridization conditions, which can be stringent or relaxed. The result of the hybridization will be a band or a pattern of bands showing that there are viral sequences incorporated into the host DNA. This information may be useful in helping to predict the occurrence of cancer. The probe can be any labelled complementary nucleic acid probe including cloned viral sequences. For RNA viruses, for example viral RNA can be used to make a DNA with reverse transcriptase; for DNA viruses, for example, viral DNA labelled by nick translation can be used. Again multiple probes can be used, especially with different labels.

Same general features apply equally to DNA and RNA viruses. Viral genomes are relatively small, so the precipitated nucleic acid is preferably collected by centrifugation; all of the procedures can use the total nucleic acid or the various procedures can be run separately. It is expected that viral nucleic acid can be concentrated by spooling cellular DNA to remove it before centrifugation. This can also be used to determine if the viral genome is integrated.

For the viral probe to hybridize, it may be necessary and at least most preferred that the probe be from the same family, genus, or species as the unknown, Reaction conditions, stringent or relaxed, may determine whether or not a given probe hybridizes a distantly related genome. The probe may be cloned viral sequences that are labeled, or may be the complete genome or a portion of it.

The technique described by Southern, supra is useful for the transfer of large DNA fragments (greater than about 0.5 kilobases) to nitrocellulose paper after alkali denaturation. This technique might be useful for DNA viruses but not for RNA viruses. RNA has been transferred and covalently coupled to activated cellulose paper (diazobenzyloxymethyl-paper), and this can be used for RNA viruses. The modification of the Southern technique by Thomas (Thomas, P., Proc. Nat. Acad. Sci., USA, 77; 5201–5205 (1980)) can be used for the efficient transfer of RNA, and small DNA fragments to nitrocellulose paper for hybridization. RNA and small DNA fragments are denatured with glyoxal and dimethyl sulfoxide, and electrophoresed in agarose gel. This procedure transfers DNA fragments between 100 and 2000 nucleotides and RNA efficiently, and they are retained on the nitrocellulose paper during hybridization. This is useful for small ribosomal DNA fragments as well. So it is most preferred to divide the restriction-enzyme digested specimen and denature the nucleic acid in one portion with glyoxal. The Southern and Thomas procedures would yield a maximum amount of information.

(2) For DNA viruses, restriction analysis can be carried out with double-stranded (DS) viral DNA's to identify viruses present. Single-stranded (SS) DNA viruses will have different genome lengths. The probe (the sequence information could be converted to DS DNA) that hybridizes, the hybridized fragment pattern and/or the sizes or size can be used to identify viruses. There are again a number of ways to obtain complementary nucleic acid probes. For example, for DS DNA nick-translation can be used; for SS DNA, DNA polymerase can be used to synthesize a cDNA.

(3) For RNA viruses, RNA is not digested by restriction endonucleases (the sequence information could be converted to DS DNA). The genomes of different RNA viruses are of different sizes, and some RNA viruses have more than 1 molecule in their genome. This, along with the base sequences detected by certain probes or pooled probes allows the RNA viruses to be identified. An example of a probe would be cDNA synthesized using viral RNA.

When searching for infectious agents in specimens it is possible to search directly by extracting nucleic acid from the specimen, or by culturing first in media or cells to increase the number of agents, or by using a concentration step such as centrifugation or trying all approaches.

The present invention lends itself readily to the preparation of "kits" containing the elements necessary to carry out the process. Such a kit may comprise a carrier being compartmentalized to receive in close confinement therein one or more container means, such as tubes or vials. One of said container means may contain unlabeled or detectably labeled nucleic acid probe, such as for example the radioactively labeled cDNA to ribosomal RNA from the organism probe, (preferably prokaryotic rRNAcDNA in the case of a kit to identify bacteria). The labeled nucleic acid probe may be present in lyophilized form, or in an appropriate buffer as necessary. One or more container means may contain one or more endonuclease enzymes to be utilized in digesting the DNA from the unknown organism. These enzymes may be present by themselves or in admixtures, in lyophilized form or in appropriate buffers. Ideally, the enzymes utilized in the kit are those for which corresponding catalogs have been prepared. Nothing stops the user, however, from preparing his or her own comparative standard at the moment of experiment. Thus, if a user suspects that an unknown is in fact of a given genus or species, he or she may prepare the band pattern for the known and compare it with the band pattern for the unknown. The kit may thus also contain all of the elements necessary in order to carry out this sub-process. These elements may include one or more known organisms, (such as bacteria), or isolated DNA from known organisms. In addition, the kit may also contain a "catalog", defined broadly as a booklet, or book, or pamphlet, or computer tape or disk, or computer access number, or the like, having the chromatographic band patterns for a variety of organisms of a certain group, such as plant species, mammal species, microbe species, especially pathologically important bacteria, insect species or the like. In this mode, a user would only need to prepare the band pattern for the unknown organism, and then visually (or by computer) compare the obtained pattern with the patterns in the catalog. The kit may also contain in one container probe rRNA for probe synthesis, in another container radiolabeled deoxyribonucleoside triphosphate, and in another container primer. In this manner the user can prepare his or her own probe rRNAcDNA.

Finally, the kit may contain all of the additional elements necessary to carry out the technique of the invention, such as buffers, growth media, enzymes, pipettes, plates, nucleic acids, nucleoside triphosphates, filter paper, gel materials, transfer materials, autoradiography supplies, and the like. It may also contain antibiotic resistance sequence probes, viral probes, or other specific character probes.

Having now generally described this invention, the same will be better understood by reference to certain specific examples which are included herein for purposes of illustration only and are not intended to be limiting of the invention, unless specified.

MATERIALS AND METHODS

A. Bacterial Experiments
Extraction of High Molecular Weight DNA

Bacterial broth cultures were centrifuged and the cells were washed with cold saline. The cells were suspended in a volume measured in ml of extraction buffer (0.15 M sodium chloride, 0.1 M EDTA, 0.03 M tris pH 8.5) approximately 10 times the gram weight of the packed cells. Lysozyme at 10 mg/ml was added to 0.5 mg/ml final concentration. The suspension was incubated at 37° C. for 30 minutes. Cell disruption was completed by the addition of 25% SDS to 2.5% final concentration, and raising the temperature to 60° C. for 10 minutes. After cooling in a tap water bath, mercaptoethanol was added to 1% final concentration. Pronase ® at 20 mg/ml in 0.02 M tris pH 7.4 was predigested at 37° C. for 2 hours and then added to 1 mg/ml final concentration. The solution was incubated at 37° C. for 18 hours. Phenol was prepared by mixing one liter redistilled phenol, 2.5 liters double distilled water, 270 ml saturated Tris base, 12 ml mercaptoethanol, and EDTA to $10^{-3}$ M final concentration and allowing the mixture to separate at 4° C. The phenol was washed with wash buffer ($10^{-1}$ M sodium chloride, $10^{-3}$ M EDTA, 10mM tris pH 8.5). Then an equal volume of fresh buffer was added. Mercaptoethanol was added to 0.1% final concentration. The solution was mixed and stored at 4° C. One half volume prepared phenol and one half volume chloroform was added to the lysed cell solution. This was shaken for approximately 10 minutes and centrifuged at 3,400×g for 15 minutes. The aqueous phase was removed with an inverted 25 ml glass pipette. The extraction procedure was repeated until there was little precipitate at the interface. One-ninth volume 2 N sodium acetate pH 5.5 was added to the aqueous phase. Two times volume of 95% ethyl alcohol at −20° C. was poured slowly down the side of the flask. The end of a Pasteur pipette was melted close and used to spool the precipitated DNA. High molecular weight DNA was dissolved in buffer ($10^{-3}$ EDTA, $10^{-2}$ M tris pH 7.4). The concentration of DNA was determined by absorbance at 260 nm using 30 micrograms per absorbance unit as conversion factor.

Restriction Endonuclease Digestion of DNA.

EcoR I restriction endonuclease reactions were performed in 0.1 M tris-HCl pH 7.5, 0.05 M NaCl, 0.005 M MgCl$_2$, and 100 micrograms per ml bovine serum albumin. EcoR I reaction mixtures contained 5 units of enzyme per microgram of DNA, and were incubated four hours at 37° C. PST I restriction endonuclease reactions were performed in 0.006 M tris-HCl pH 7.4, 0.05 M sodium chloride, 0.006 M magnesium chloride, 0.006 M 2-mercaptoethanol, and 100 micrograms per ml of bovine serum albumin. PST I reaction mixtures contained 2 units of enzyme per microgram DNA, and were incubated four hours at 37° C. Usually 10 micrograms DNA was digested in a final volume of 40 microliters. Ten times concentration buffers were added. Sterile distilled water was added depending on the volume of DNA. λ Bacteriophage DNA was restricted with EcoR I to provide marker bands for fragment size determinations. Usually 2 micrograms λ DNA was digested with 20 units EcoR I in a final volume of 20 microliters.

Gel Electrophoresis and DNA Transfer.

DNA digests were supplemented with glycerol, to about 20%, and bromophenol blue tracking dye. In the case of λ DNA digests, 20 microliters of 1x EcoR I buffer was added to each 20 microliter reaction mixture. Usually 15 microliters 75% glycerol and 5 microliters 0.5% bromophenol blue were added to each 40 microliter reaction mixture.

10 micrograms digested bacterial DNA or 2 micrograms digested λDNA were loaded per well and overlaid with molten agarose. Digests were electrophoresed in 0.8% agarose with 0.02 M sodium acetate, 0.002 M EDTA, 0.018 M tris base, and 0.028 M tris HCl pH 8.05 at 35 V until the dye migrated 13 to 16 cm. Gels were then immersed in ethidium bromide (0.005 mg/ml) and placed on a UV-light box to visualize the λ fragments. DNA was transferred to nitrocellulose filter paper by the method of Southern, supra. Gels were treated with denaturing solution (1.5 M sodium chloride, 0.5 M sodium hydroxide) on a rocker table for 20 min. Denaturing solution was replaced with neutralization solution (3.0 M sodium chloride, 0.5 M tris HCl, pH 75), and after 40 minutes the gels were checked with pH paper. Following neutralization, the gels were treated with 6 x SSC buffer (SSC=0.15 M sodium chloride, 0.015 M sodium citrate) for 10 minutes. DNA fragments were transferred from the gel to the nitrocellulose paper by drawing 6 X SSC through the gel and nitrocellulose paper with a stack of paper towels for 15 hours. Filters were placed between two sheets of 3 MM chromatography paper, wrapped in aluminum foil, shiny side out, and dried in a vacuum oven at 80° C. for 4 hours.

Synthesis of $^{32}$P ribosomal RNA Complementary DNA ($^{32}$P rRNA cDNA).

$^{32}$P-labeled DNA complementary to E. coli R-13 23S and 16S ribosomal RNA was synthesized using reverse transcriptase from avian myeloblastosis virus (AMV). The reaction mixture contained 5 microliters 0.2 M dithiothreitol, 25 microliters 1 M tris pH 8.0, 8.3 microliters 3 M potassium chloride, 40 microliters 0.1 M magnesium chloride, 70 micrograms actinomycin, 14 microliters 0.04 M dATP, 14 microliters 0.04 M dGDP, 14 microliters 0.04 M dTTP and 96.7 microliters H₂O. The following were added to a plastic tube: 137.5 microliters reaction mixture, 15 microliters calf thymus primer (10 mg/ml), 7 microliters H 20, 3 microliters rRNA (using 40 micrograms/OD unit concentration, is 2.76 micrograms/microliters), 40 microliters deoxycytidine 5'-($^{32}$P) triphosphate (10 mCi/ml), and 13 microliters AMV polymerase (6,900 units μl. The enzymatic reaction was incubated 1.5 hours at 37° C. Then the solution was extracted in 5 ml each of chloroform and prepared phenol. After centrifugation (JS 13,600 RPM), the aqueous phase was layered directly on a Sephadex ® G-50 column (1.5×22 cm). A plastic 10 ml pipette was used for the column. A small glass bead was placed in the tip, rubber tubing with a pinch clamp was attached, and degassed G-50 swelled in 0.05% SDS overnight was added. The aqueous phase was allowed to flow directly into the G-50 and was then eluted with 0.05% SDS. 20 fractions at 0.5 ml each were collected in plastic vials. Tubes containing peak fractions were detected by Cerenkov counting using a $^3$H discriminator, counting for 0.1 min. per sample and recording total counts. Peak fractions were pooled. Aliquots were added to Aquesol ® (commercially available), and the CPM of $^{32}$P per ml was determined by scintillation counting.

Hybridization and Autoradiography.

Fragments containing ribosomal RNA gene sequences were detected by autoradiography after hybridization of the DNA on the filters to $^{32}$P-rRNA cDNA. Filters were soaked in hybridization mix (3 x SSC, 0.1% SDS, 100 micrograms/ml denatured and sonicated canine DNA, and Deinhart's solution (0.2% each of bovine serum albumen, Ficoll, and polyvinyl pyrrolidine)), for 1 hour at 68° C. $^{32}$P rRNA CDNA was added at 4×10⁶ CPM/ml, and the hybridization reaction was incubated at 68° C. for 48 hours. Filters were then washed in 3×SSC, and 0.1% SDS at 15 min. intervals for 2 hours or until the wash solution contained about 3,000 cpm $^{32}$P per ml. Filters were air dried, wrapped in plastic wrap and autoradiographed approximately 1 hour with Kodak X-OMAT R film at −70° C.

B. Mammalian Experiments.

*Mus musculus domesticus* (mouse) rRNA probes were synthesized from 18S and 28S, and only 28S rRNA. Nucleic acid was extracted from mouse liver and precipitated. High molecular weight DNA was spooled and removed. The remaining nucleic acid was collected by centrifugation and dissolved in buffer, 50 mM MgCl₂ and 100 mM Tris pH 7.4. DNAse (RNAse free) was added to a concentration of 50μg/ml. The mixture was incubated at 37° C. for 30 min. The resulting RNA was reextracted, ethanol precipitated, and disolved in 1 mM sodium phosphate buffer pH 6.8. A 5 to 20% sucrose gradient in 0.1 M Tris pH 7.4 and 0.01 M EDTA was prepared. The sample was added and the gradients spun in an SW40 rotor 7 hr. at 35K RPM. Fractions were collected by optical density. The 18S and 28S fractions were selected by comparison to known molecular weight markers.

For all of the mammalian experiments relaxed hybridization conditions were used, 54° C. The washing procedure, carried out at 54° C, was 3 separate washes with 3xSSC with 0.05% SDS for 15 min. each.

EXAMPLE 1

Bacterial Species are Defined by Restriction Endonuclease Analysis of Ribosomal RNA Genes The several strains of *P. aeruginosa* used in this example have the minimal phenotypic characters which identify the species (Hugh R. H., et al, in: Manual of Clinical Microbiology, 2d Ed. ASM, 1974, pp. 250-269). (Table 2). Strains of three other Pseudomonas and two Acinetobacter species were selected to compare species and genera (Table 3).

TABLE 2

Corresponding strain numbers of isolates with the minimal phenotypic characters of *P. Aeruginosa* for the comparison of Strains.

| RH | ATCC |
|---|---|
| 151 | 10752 |
| 809 | 7701 |
| 810 | 8689 |
| 811 | 8707 |
| 812 | 8709 |
| 815 | 10145 |
| 1559 | 14425 |

Strains used for comparison of Pseudomonas and Acinetobacter species are listed in Table 3.

TABLE 3

Corresponding strain numbers of type, neotype and reference strains for the comparison of species and genera

| Species | RH | ATCC | NCTC | Strain status |
|---|---|---|---|---|
| P. aeruginosa | 815 | 10145 | 10332 | type |
| P. stutzeri | 2601 | 17588 | | neotype |
| P. fluorescens | 818 | 13525 | 10038 | neotype |
| P. putida | 827 | 12633 | | neotype |
| A. anitratus | 2208 | 19606 | | type |
| A. lwoffii | 462 | 7976 | | reference |

Acinetobacter species were selected for comparison of genera because they share certain attributes with many Pseudomonas species.

The sizes (kilobase pairs) of fragments in EcoR I digests are: *P. stutzeri* 16.0, 12.0, 9.4; *P. fluorescens* 16.0, 10.0, 8.6, 7.8, 7/0; *P. putida* 24.0, 15.0, 10.0, 8.9; *A. anitratus* 20.0, 15.0, 12.5, 9.8, 7.8, 6.1, 5.2, 4.8, 3.8, 2.8 (size of the smallest 3 fragments not calculated); *A. lwoffi* 12.0, 10.0, 9.1, 7.0, 6.4, 5.7, 5.5, 5.3, 4.8, 4.4, 3.6, 3.2, 2.9 (size of the smallest 3 fragments not calculated). The sizes (kilobase pairs) of fragments in PST I digests are; *P. stutzeri* 6.7, 6.1, 5.5; *P. fluorescens* 10.0, 9.4, 7.8, 7.0; *P. putida* 10.5, 9.9, 6.8, 6.3, 4.4; *A. anitratus* 36.0, 28.0, 20.5, 12.0, 10.0, 5.8, 3.7, 2.6, 2.4; *A. lwoffi* 9.9, 8.7, 7.2, 5.7, 4.0, 3.6, 3.2, 2.7.

Figure 2:
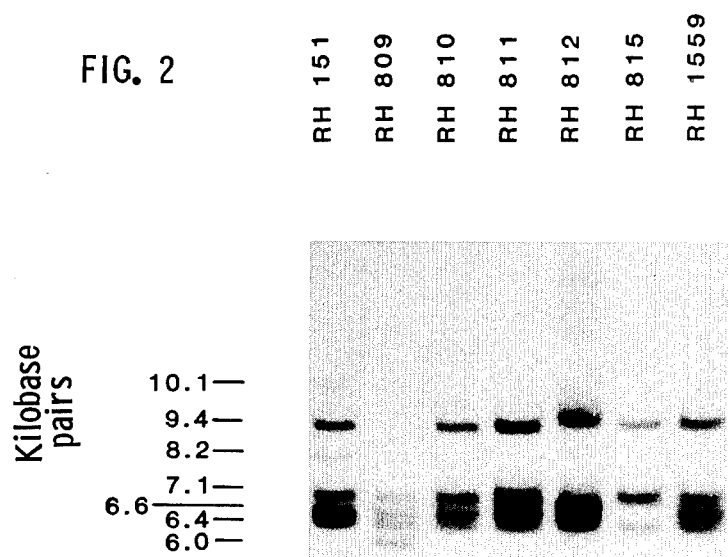
FIG. 2 shows the Pst I restriction endonuclease digest of DNA isolated from strains of *P. aeruginosa*, using cDNA to 16S and 23S rRNA of *E. coli* as the probe.

Comparison of the hybridized restriction fragments from the seven strains of *P. aeruginosa* leads to the conclusion that this species can be defined by an EcoR I specific set of fragments containing rRNA gene sequences, 10.1, 9.4, 7.6, and 5.9 kilobase pairs (KBP) (FIG. 1). The 7.6 KBP EcoR I fragment occurs in 4 of the 7 strains in this sample. An analogous situation occurs among certain phenotypic characters of strains of species. The fact that the EcoR I sets of fragments from the 7 strains can be used to separate the strains into two groups prompts speculation that there may be two species with the minimal phenotypic characters of *P. aeruginosa*. The results of experiments in which DNA was digested with Pst I (FIG. 2) lead to the conclusion that the strain variation shown by the EcoR I 7.6 KBP fragment represents variation within the species, since there is a single conserved set of PST I fragments, 9.4, 7.1, 6.6, and 6.4 KBP, that define the species. The 9.4 and 6.6 KBP Pst I fragments occur in 6 of the 7 strains of *P. aeruginosa*; the 7.1 and 6.4 KBP PST I fragments occur in all of the strains sampled. PST I fragment variation occurs in strains that do not contain an EcoR I 7.6 KBP fragment; RH 151 has 10.1 and 8.2 KBP fragments, RH 809 does not contain a 9.4 KBP fragment and has a 6.0 KBP fragment, and RH 815; the type strain, does not contain a 6.6 KBP fragment. The patterns of hybridized fragments support the conclusion that enzyme specific, conserved sets can be used to define species. Strains of a species probably have a majority of the fragments in the conserved set. The occurrence of fragment variations in some strains does not prevent identification and may prove useful in epidemiological studies.

Figure 3:
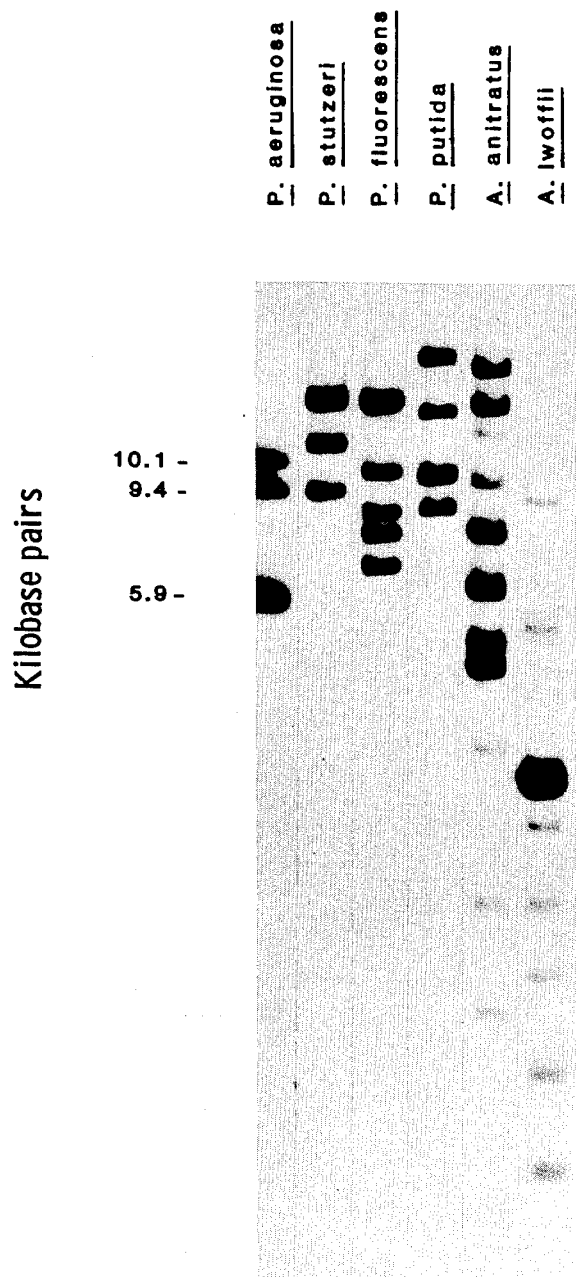
FIG. 3 shows the EcoR I restriction endonuclease digest of DNA isolated from species of glucose-nonfermenting, gram-negative rods, using cDNA to 16S and 23S rRNA of *E. coli* as the probe.
Figure 4:
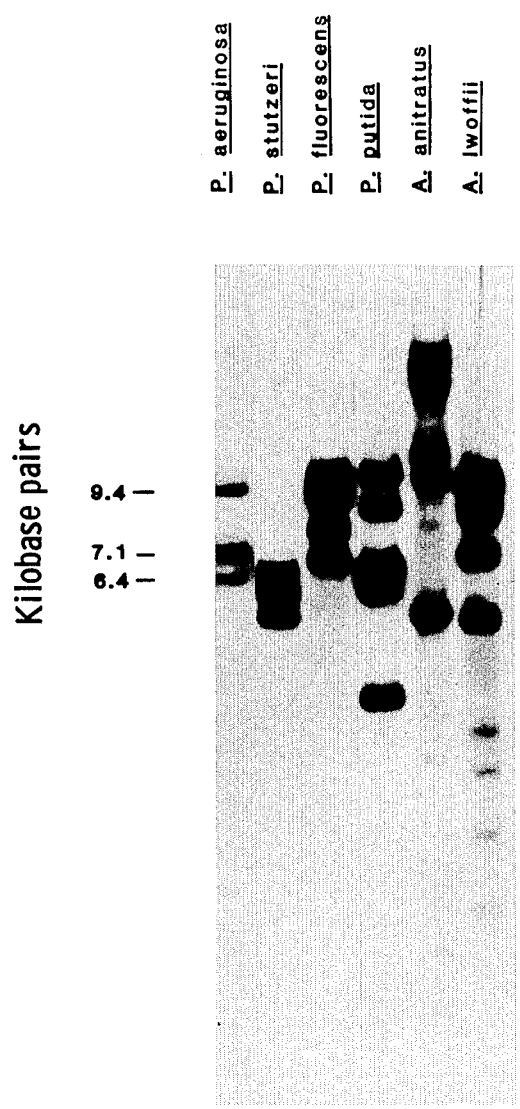
FIG. 4 shows the Pst I restriction endonuclease digest of DNA isolated from species of glucose-nonfermenting, gram-negative rods using cDNA to 16S and 23S rRNA of *E. coli* as the probe.

The occurrence of variation, EcoR I 7.6 KBP fragment in *P. aeruginosa* strains, may be put into perspective by examining hybridized EcoR I fragments found in the type strains of other Pseudomonas species (FIG. 3). The type strains of *P. stutzeri*, *P. fluorescens*, and *P. putida* do not contain a 7.6 KBP fragment, but do have EcoR I fragments of the same size in common; *P. aeruginosa* and *P. stutzeri* each have a 9.4 KBP fragment, *P. stutzeri* and *P. fluorescens* each have a 16 KBP fragment, and *P. fluorescens* and *P. putida* each have a 10 KBP fragment. In general, the sizes of the fragments are unique in the type strains of each of the 4 Pseudomonas species; and the type strain of each species has a different size range of fragments. These general comments are also true for the PST I digests (FIG. 4).

When the fragment patterns of one strain of each of the 4 Pseudomonas and 2 Acinetobacter species are compared, it can be concluded that the species of each genus are similar, but the genera differ. The 2 Acinetobacter species have a greater range of hybridized fragment sizes than do the 4 Pseudomonas species.

Without the aid of restriction enzyme maps such as those available for *E. coli*, *Bacillus thuringiensis* and *B subtilis*, it is not possible to predict where enzymes cut rRNA genes the number of copies per genome, whether there are heterologous flanking regions between genes, or gene heterogeneity. The *E. coli* rRNAcDNA probe may fail to hybridize with some restriction fragments containing rRNA gene sequences, and if so, this reflects the evolutionary distance or diversity between the test organism and *E. coli*. The conserved nature of rRNA can be used to argue that this is not the case. However, this is a minor problem compared to the advantage of having a standard probe that can be equally applied to any unknown species.

EXAMPLE 2

Comparison of Restriction Analysis with DNA-DNA Liquid Hybridization

The strains used in this study are listed in Tables 4 and 5.

TABLE 4

Corresponding Strain Numbers of Neotype strains of *B. subtilis* and type strains of junior synonyms

| Species | RH | ATCC | Strain status |
|---|---|---|---|
| *B. subtilis* | 3021 | 6051 | neotype |
| *B. uniflagellatus* | 2990 | 15134 | type |
| *B. amyloliquafaciens* | 3061 | 23350 | type |

TABLE 5

Corresponding strain number of strains of *B. Subtilis*

| RH | NRRL | ATCC |
|---|---|---|
| 3063 | B-354(NRS-231) | 6633 |
| 3064 | B-356(NRS-238) | 7067 |
| 3065 | NRS-265 | 6455 |
| 3066 | NRS-659 | 7060 |
| 3067 | NRS-730 | 7003 |
| 3068 | NRS-737 | 943 |
| 3069 | NRS-741 | 4344 |
| 3070 | NRS-773 | 8188 |
| 3071 | NRS-1106 | 4944 |
| 3072 | NRS-1107 | 7480 |

High molecular weight DNA was isolated from each of the strains. Liquid DNA-DNA hybridization data was colleccted using RH 3021 and RH 2990 labeled DNAs and results are shown in Table 6.

TABLE 6

Percent hybridization between labeled DNA probe and DNA from strains of *B. subtilis*

| | Labeled DNA | | | | | | | | | | | | |
|---|---|---|---|---|---|---|---|---|---|---|---|---|---|
| probe | RH 3063 | RH 3064 | RH 3066 | RH 3067 | RH 3068 | RH 3065 | RH 3069 | RH 3070 | RH 3071 | RH 3072 | RH 3021 | RH 2990 | RH 3061 |
| RH 3021 | 61 | 77 | 51 | 96 | 84 | 18 | 14 | — | 93 | 15 | 100 | 20 | 11 |
| RH 2990 | 12 | 10 | 13 | 15 | 16 | 50 | 100 | — | 17 | 100 | 20 | 100 | 70 |

Figure 5:
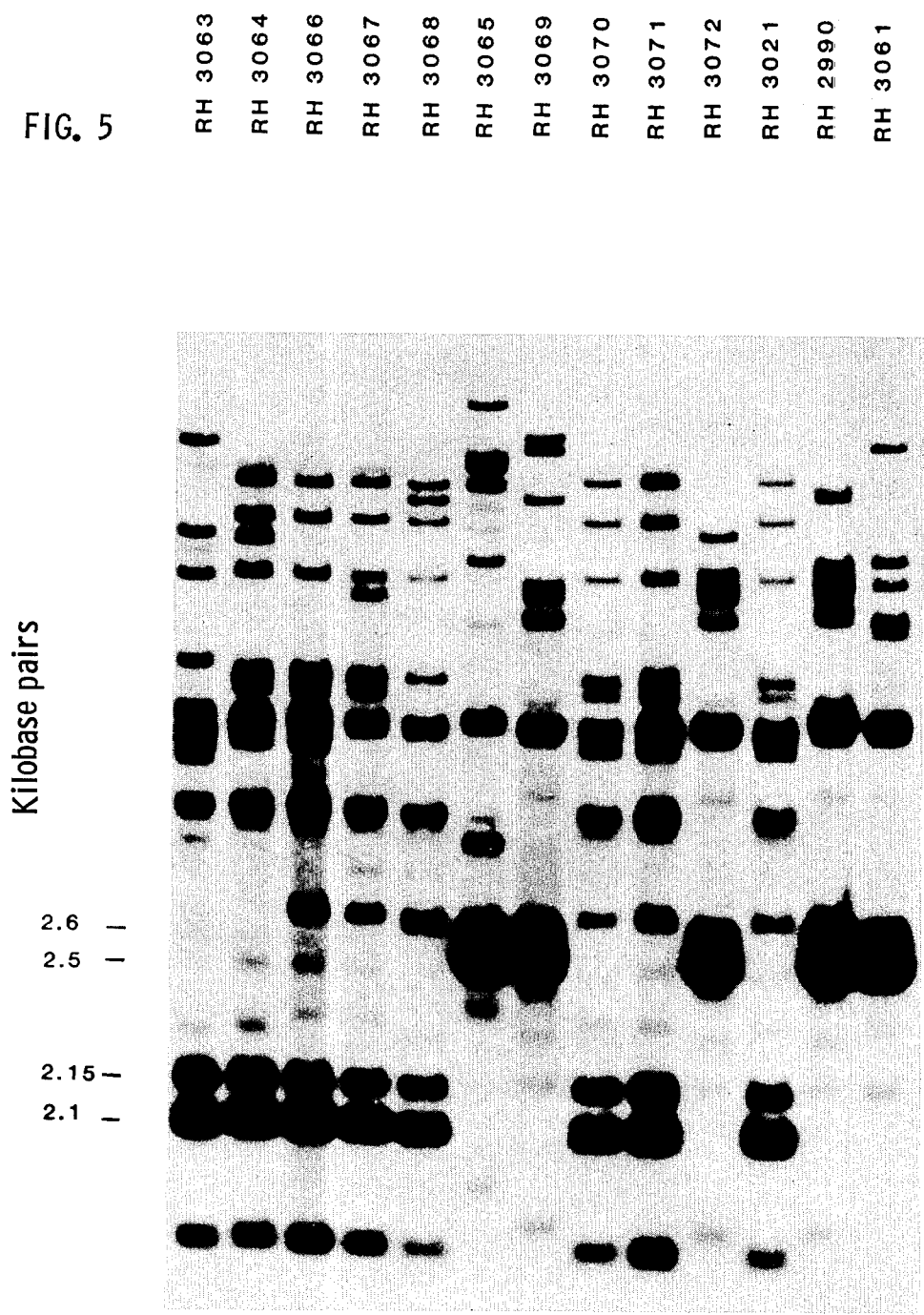
FIG. 5 shows the EcoR I restriction endonuclease digest of DNA isolated from various *Bacillus subtilis* strains, using cDNA to 16S and 23S rRNA of *E. coli* as the probe.
Figure 6:
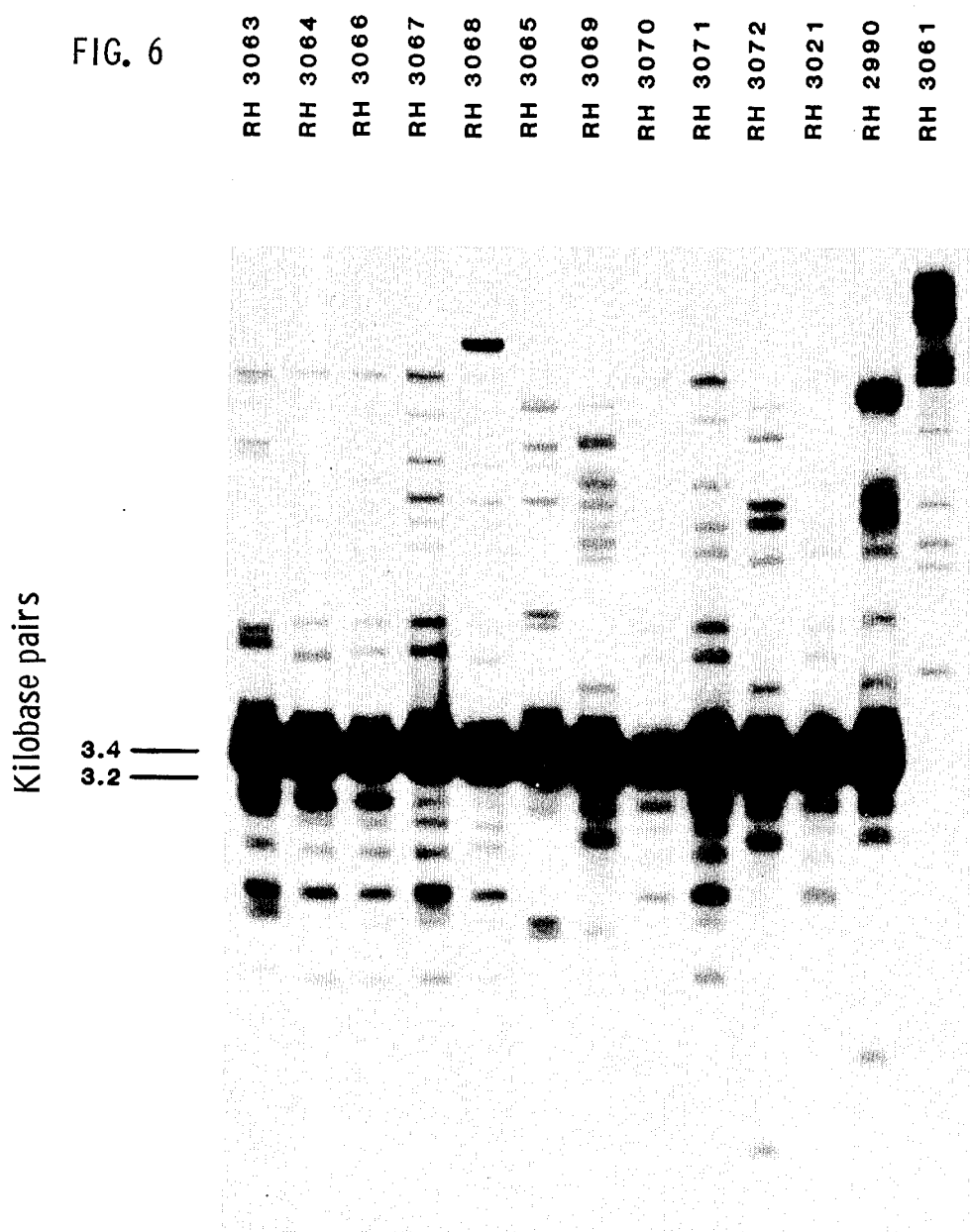
FIG. 6 shows the Pst I data for the same strains as in FIG. 5, with the same probe.
Figure 7:
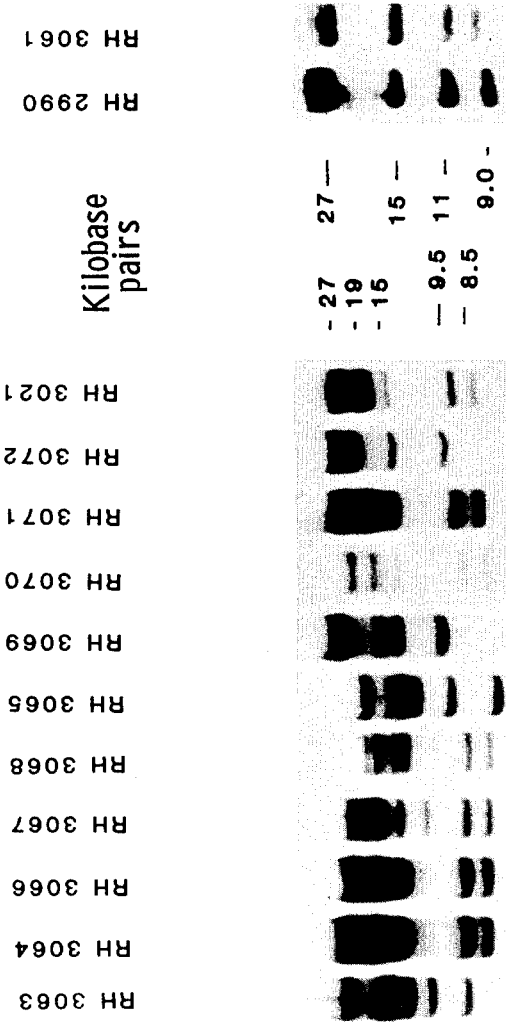
FIG. 7 shows the Bgl II data for the same strains as in FIGS. 5 and 6, with the same probe.
Figure 8:
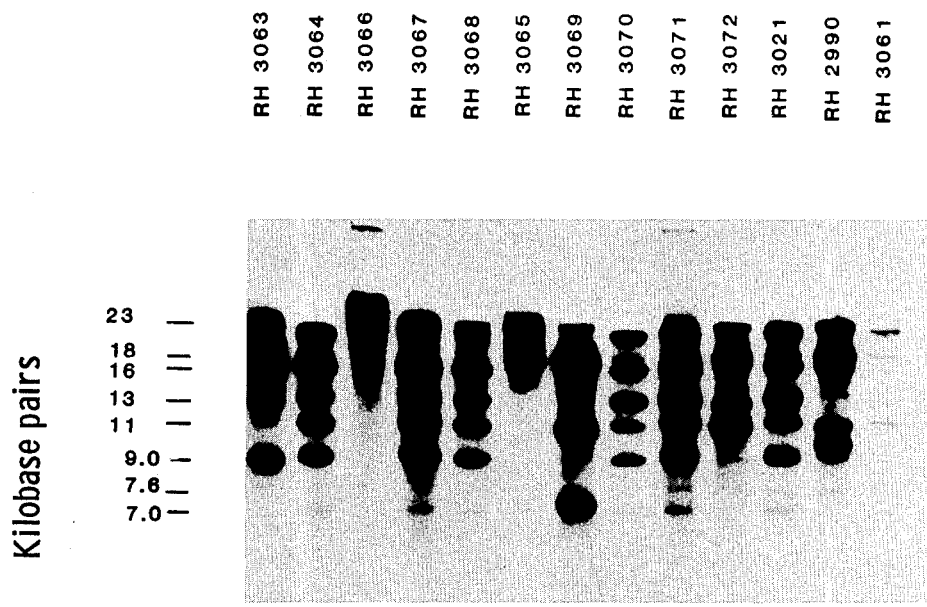
FIG. 8 shows the Sac I data for the same strains as in FIGS. 5-7, with the same probe.

The data shows there are two hybridization groups. Similar data is reported in the literature for *B. subtilis* (Seki et al, International Journal of Systematic Bacteriology, 25:258–270 (1975)). These two groups can be represented by RH 3021 and RH 2990. When restriction endonuclease analysis of ribosomal RNA genes is carried out, the EcoR I digests (FIG. 5) can be separated into two groups. The group represented by RH 3021 has two intensely hybridized fragments (2.15 and 2.1 KBP). The group represented by RH 2990 has two intensely hybridized fragments (2.6 and 2.5 KBP). The EcoR I data can be used to place *B. subtilis* strains in appropriate DNA-DNA hybridization groups. According to the DNA-DNA hybridization 70% rule, *B. subtilis* is actually two species. However, when the PST I data (FIG. 6) is considered, it is possible to think of the groups as two divergent populations related to a common ancestor or speciation event. The conclusion that *B. subtilis* is one species correlates with phenotypic data. The strains listed in Table 5 are identified as *B. subtilis* in Gordon, R. E. et al "The Genus Bacillus", Agriculture Handbook No. 427, Agricultural Research Service, U.S. Dept. of Agriculture, Washington, D.C. pp. 36–41. Restriction analysis can provide data which is comparable to DNA-DNA hybridization data, or by selecting the proper enzyme, restriction analysis can adequately define species despite divergence. RH 3061 has lost PST I sites. However, the EcoR I data suggests that the strain is *B. subtilis*. The same is concluded from the Bgl II data (FIG. 7) and Sac I data (FIG. 8).

EXAMPLE 3

Stability of the Restriction Analysis Pattern and Other *Bacillus polymyxa* Experiments

TABLE 7

| Species | Neotype strains of *B. Subtilis* and *B. Polymyxa* | | | |
|---|---|---|---|---|
| | RH | ATCC | NRRL | Comments |
| *B. subtilis* | 3021 | 6051 | | neotype |
| *B. polymyxa* | 3074 | 842 | | neotype |
| *B. polymyxa* | 3033 | | | asporogenous mutant derived from RH 3074 |
| *B. polymyxa* | 3062 | | NRS-1105 | neotype |
| *B. polymyxa* | 3073 | | | asporogenous mutant derived from NRS-1105 |

Figure 10:
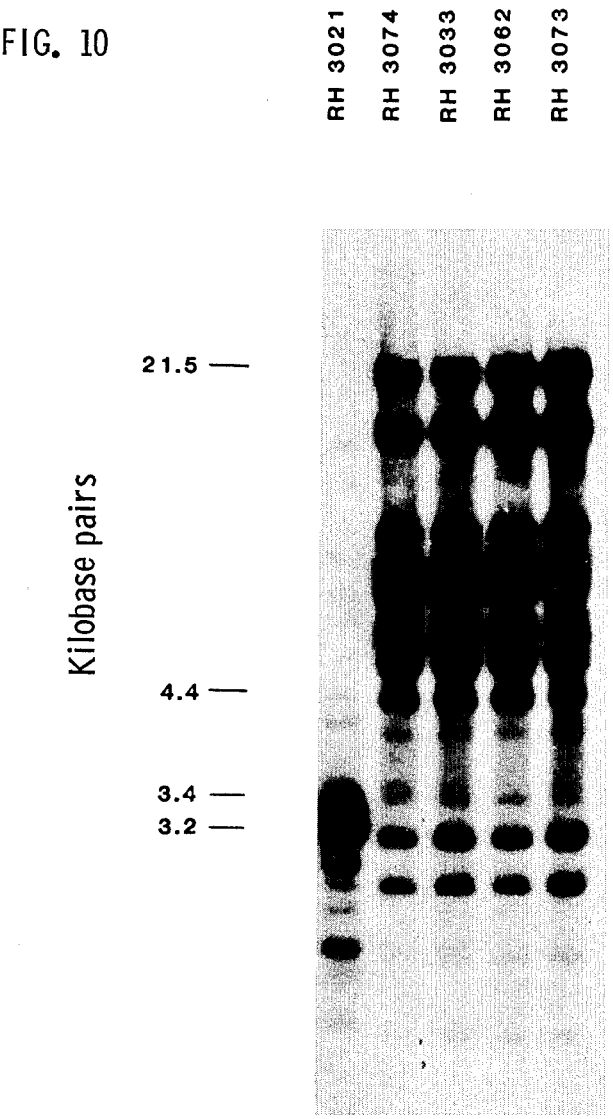
FIG. 10 shows the Pst I data for the same strains as in FIG. 9 with the same probe.
Figure 11:
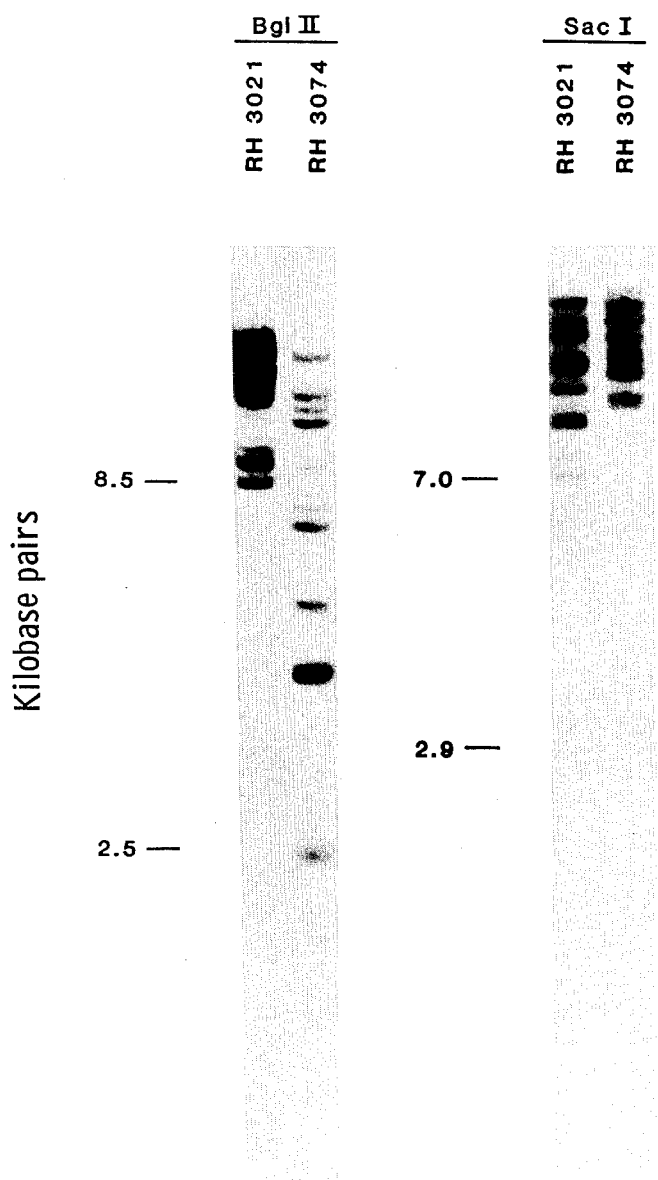
FIG. 11 shows the Bgl II and Sac I data for the same strains as in FIGS. 9 and 10, with the same probe.

*B. subtilis* and *B. polymyxa* can be distinguished by EcoR I data (FIG. 9), PST I data (FIG. 10), Bgl II data (FIG. 11, left) and Sac I data (FIG. 11, right). It can be concluded from the major differences in the PST I band patterns, that *Bacillus polymyxa* is in the wrong genus. While both species produce spores, they are not phenotypically similar. It is reassuring that the type strain of *B. polymyxa* from both culture collections, ATCC and NRRL, have the same band patterns. The important data, however, is that the asporogenous mutants can be identified. It is very difficult, perhaps impossible, to identify Bacillus species if they fail to form spores.

EXAMPLE 4

Identification of a Bacterial Species In Mouse Tissue Without Isolation

Figure 12:
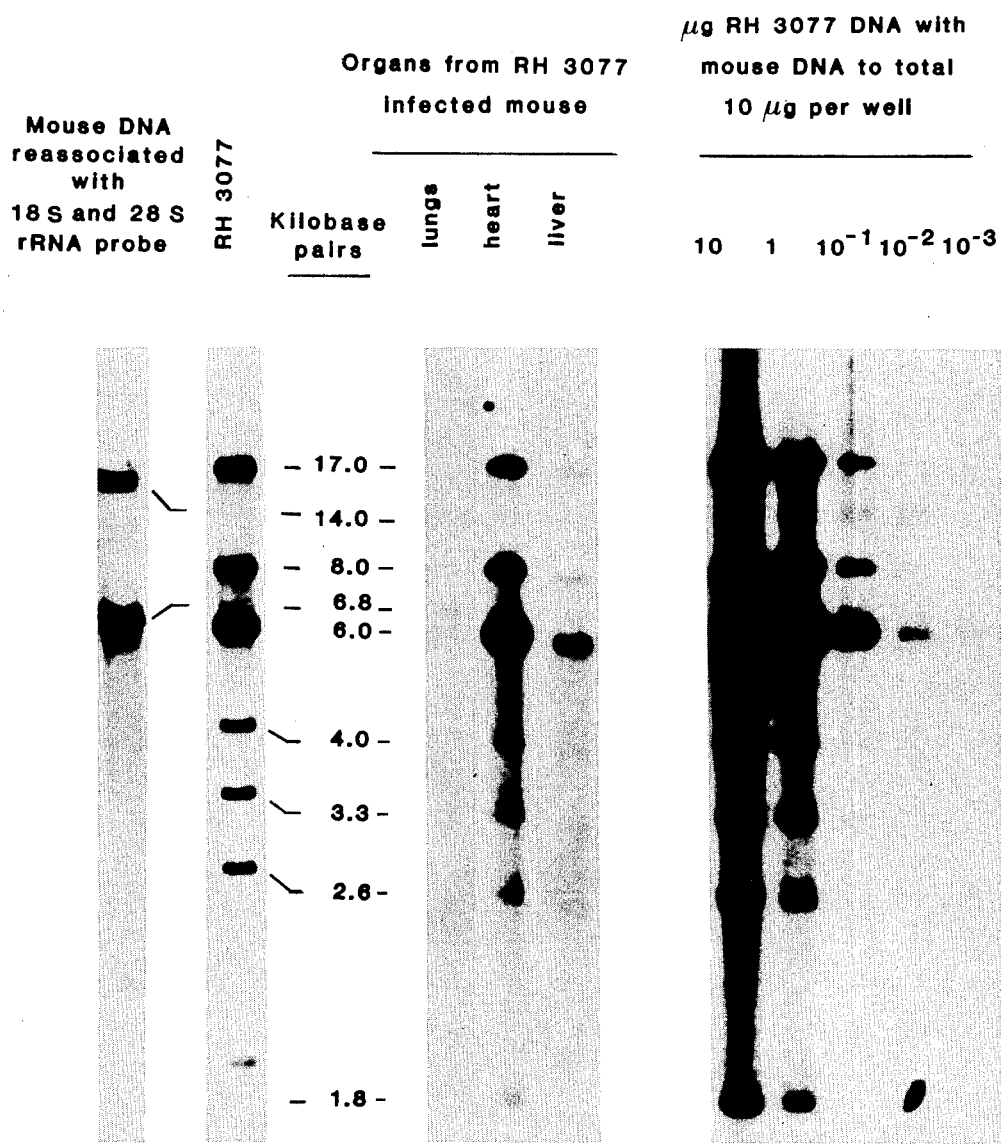
FIG. 12 shows the detection of *Streptococcus pneumoniae* in EcoR I digested DNA from infected mouse tissues using cDNA from 16S and 23S rRNA from *E. coli* as the probe.

A Swiss mouse, *Mus musculus domesticus* (inbred strain), was inoculated intraperitoneally with 0.5 ml of a turbid suspension of *Streptococcus pneumoniae* RH 3077 (ATCC 6303). When the mouse became moribund, the heart, lungs, and liver were removed. High molecular weight DNA was isolated from these tissues, *S. pneumoniae* RH 3077, and Swiss mouse organs, and the procedure for restriction endonuclease analysis of rRNA genes was carried out using EcoR I to digest the DNAs. In addition to washing the filters in 3×SSC, they were washed for 2×15 minutes periods in 0.3×SSC and 0.05% SDS. Autoradiography was carried out for 48 hr. The data (FIG. 12), shows that *S. pneumoniae* can be defined by seven hybridized fragments (17.0, 8.0, 6.0, 4.0, 3.3, 2.6 and 1.8 KBP). The bacterial cDNA probe hybridizes poorly to two mouse DNA fragments (14.0 and 6.8 KBP). Hybridized fragments signal the presence of *S. pneumoniae* in the infected tissues. All seven bands can be seen in the heart DNA extract. They are less intense in the liver DNA extract, but all can be seen in the autoradiograph. Only the 6.0 KBP band appears in the lung DNA extract. The lesser number of bacteria in the lungs can be explained by the mouse having septicemia rather than pneumonia. The lungs showed no consolidation at autopsy. In order to determine the sensitivity of the assay, bacterial DNA was diluted with mouse DNA and electrophoresed. All seven bands can be seen in the autoradiograph when 0.1 micrograms of bacterial DNA is used. The 17.0, 8.0 and 6.0 KBP bands can be seen with $10^{-3}$ μg of bacterial DNA. If the figure of $5 \times 10^{-3}$ μg DNA per $10^6$ *S. pneumoniae* cells is used (Biochim Biophys Acta 26:68), $10^{-1}$ μg is equivalent to $2 \times 10^7$ cells. The present technique is thus useful for diagnosing infections at this level of sensitivity.

Figure 9:
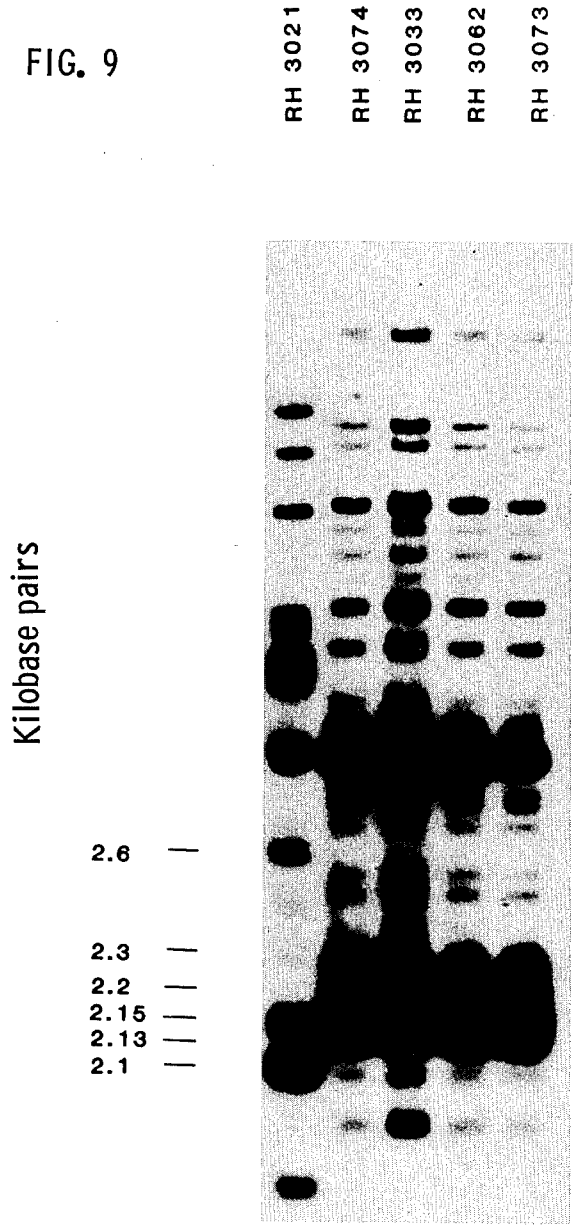
FIG. 9 shows the EcoR I restriction endonuclease digest of DNA isolated from *B. subtilis* and *B. polymyxa*, using cDNA to 16S and 23S rRNA from *E. coli* as the probe.

This Example also demonstrates that the bacterial probe hybridizes with mouse-specific EcoR I fragments (see FIG. 9, fragments having 14.0 and 6.8 KBP). These fragments correspond to EcoR I fragments detected by mouse 18S and 28S ribosomal RNA probe. (FIG. 14 infra shows that the 6.8 KBP fragment contains the 28S rRNA sequences). The bacterial probe does not hybridize as well to mammalian ribosomal RNA gene sequences, so the bands are less intense, the system of bacterial probe and nuclear mammalian DNA is less sensitive, and selectivity for DNA from infecting prokaryotes is clearly demonstrated. In experiments where bacterial probe was hybridized to 10 μg digested bacterial DNA per lane, no hybridization to 10 μg digested human or mouse DNA per lane was detected on the autoradiographs when the bacterial bands were clearly seen.

EXAMPLES 5–8

Mammalian experiments

These examples illustrates that the concept of rRNA restriction analysis to identify organisms can be successfully applied not only to bacteria but to complex, eukaryotic organisms.

Figure 13:
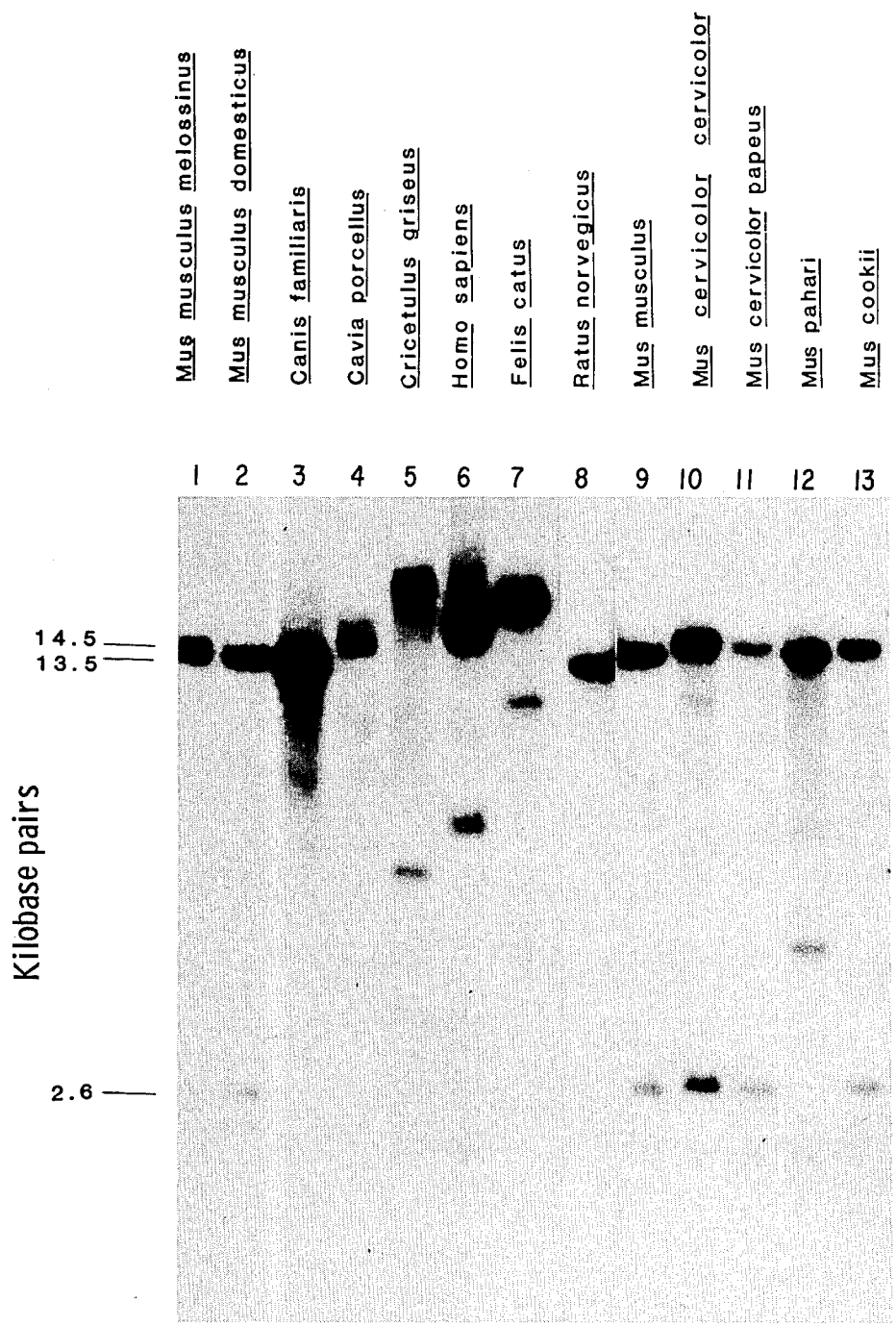
FIG. 13 shows the identification of a mouse species by comparing Pst I digests of DNA isolated from mammalian tissues, using cDNA to 18S and 28S rRNA from cytoplasmic ribosomes of *Mus musculus domesticus* (mouse).

FIG. 13 shows that mammalian genera can be recognized with *Mus musculus domesticus* 18S and 28S rRNA probe, and that several species of Mus can be distinguished. In this Figure the enzyme is PST I, and the subjects and corresponding bands are as follows:

1. *Mus musculus melossinus* (mouse) 14.5, 13.5, 2.6
2. *Mus musculus domesticus* (mouse) 13.5, 2.6
3. *Canis familiaris* (dog) 12.0
4. *Cavia porcellus* (guinea pig) 17.0, 14.0, 13.0, 8.8, 5.7, 4.7 and one band less than 3.0
5. *Cricetulus griseus* (hamster) 25.0, 4.7
6. *Homo sapiens* (human) 15.0, 5.7
7. *Felis catus* (cat) 20.0, 9.7
8. *Ratus norvegicus* (rat) 12.5
9. *Mus musculus domesticus* (mouse) 13.5, 2.6
10. *Mus cervicolor cervicolor* (mouse) 14.0, 2.7
11. *Mus cervicolor papeus* (mouse) 13.5, 2.6
12. *Mus pahari* (mouse) 13.0, 3.7
13. *Mus cookii* (mouse) 13.5, 2.6

Figure 14:
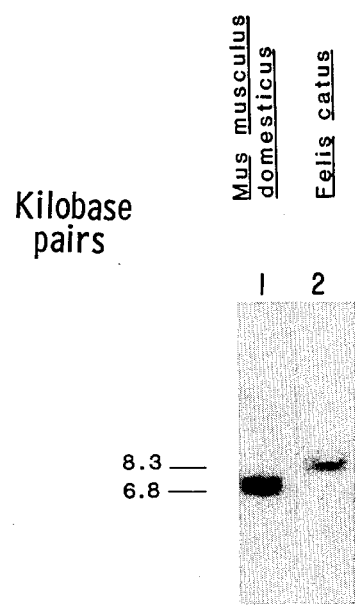
FIG. 14 shows the EcoR I digested DNA from mouse and cat tissues hybridized with *Mus musculus domesticus* 28S rRNA cDNA probe.

FIG. 14 shows that mouse and cat DNA can be distinguished by the 28S rRNA cDNA alone, and that the pattern of hybridized bands is dependent on the composition of the probe sequences. In FIG. 14 the enzyme is EcoR I, and the subjects and bands are as follows:

1. *Mus musculus domesticus* (mouse) 6.8 KBP
2. *Felis catus* (cat) 8.3 KBP

Figure 15:
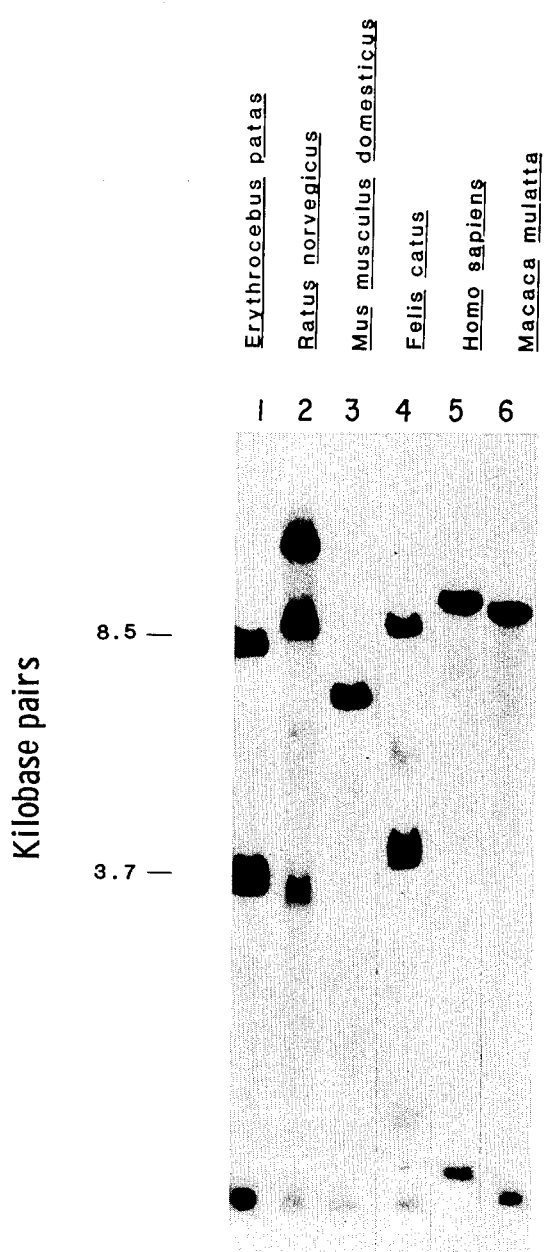
FIG. 15 shows Sac I digested DNA from mammalian tissues hybridized with *Mus musculus domesticus* 18S and 28S rRNA cDNA probe.

In FIG. 15 the enzyme is Sac I, and the subjects and bands are as follows:

1. *Erythrocebus patas* (patas monkey) 8.5, 3.7, <3.0
   *Ratus norvegicus* (rat) 25.0, 9.5, 3.6<3.0
2. *Mus musculus domesticus* (mouse) 6.8, <3.0
3. *Felis catus* (cat) 9.5, 5.3, 4.0, <3.0, <3.0
4. *Homo sapiens* (human) 10.5, <3.0
5. *Macaca mulatta* (rhesus monkey) 9.8, <3.0

When FIG. 15 (Sac I digests) is compared to the other mammalian figures it can be seen that the hybridized pattern is enzyme specific.

Figure 16:
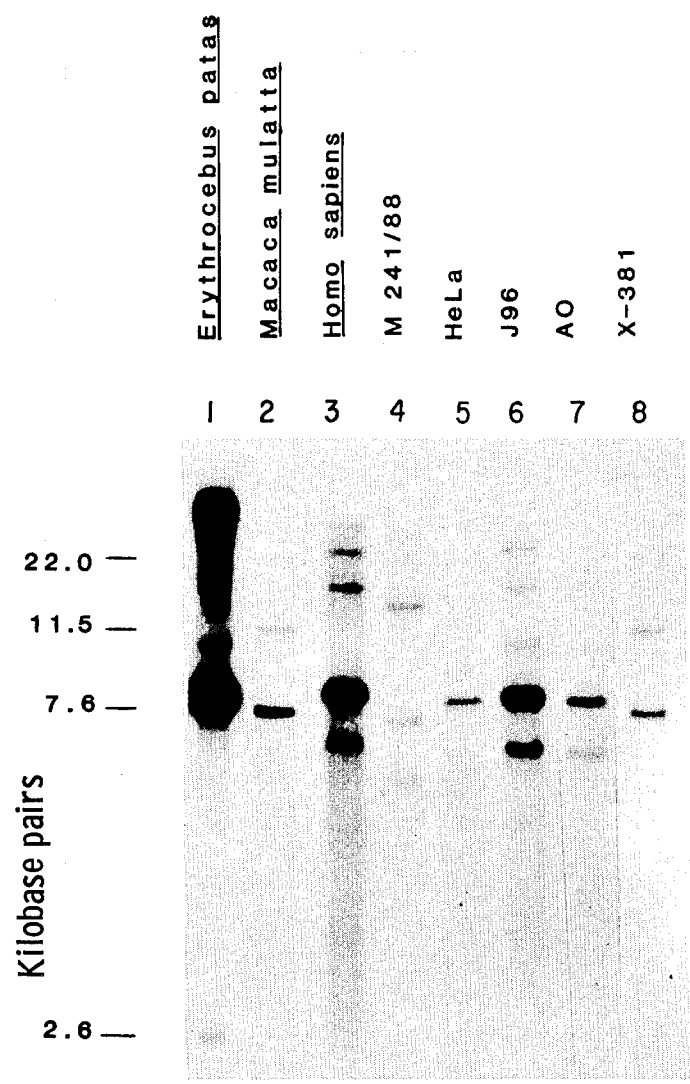
FIG. 16 shows EcoR I digested DNA from mammalian tissues and cell cultures hybridized with *Mus musculus domesticus* 18S and 28S rRNA cDNA probe.

FIG. 16 shows that primates can be distinguished. Cell cultures have bands in common with tissue from the species of origin, and different human cell cultures can be distinguished by additions and deletions of bands. In this figure, the enzyme is EcoR I, and the subjects and bands are as follows:

1. *Erythrocebus patas* (patas monkey) >22.0, 11.0, 7.6, 2.6
2. *Macaca mulatta* (rhesus monkey) 22.0, 11.5, 7.6

3. *Homo sapiens* (human) >22.0, 22.0, 16.0, 8.1, 6.6
4. M 241/88 (langur monkey cell culture) 14.0, 7.2, 5.7
5. HeLa (human cell culture) 8.1, 6.6
6. J96 (human cell culture) >22.0, 22.0, 16.0, 11.0, 8.1, 6.6
7. AO (human cell culture) 22.0, 16.0, 8.1, 6.6
8. X-381 (rhesus monkey) 22.0, 11.5, 7.6

Having now fully described this invention, it will be apparent to one of ordinary skill in the art that many variations and permutations can be carried within a wide range of equivalents without effecting the spirit or scope of the invention, or of any embodiments thereof.

What is claimed as new and intended to be covered by Letters Patent of the United States is:

1. A method of establishing the species of an unknown organism which comprises:
   (1) providing as chromatographic pattern representing the hybridization of ribosomal RNA information containing nucleic acid from or derived from a known probe organism to restriction endonuclease-digested DNA from an unknown organism,
   (2) comparing said pattern with a number of additional chromatographic patterns sufficient to enable the establishment of such species; each one of said additional chromatographic patterns representing the hybridization of ribosomal RNA information-containing nucleic acid from or derived from said known probe organism to restriction endonuclease-digested DNA from a known different organism species; and
   (3) establishing the species of said unknown organism by means of a set of ribosomal RNA sequence-containing restriction fragments present in said chromatographic pattern of said unknown organism; said set being conserved among different strains of said species but not conserved among different species.

2. The method of claim 1 wherein said ribosomal RNA information-containing nucleic acid is detectably labeled.

3. The method of claim 2 wherein said ribosomal RNA information-containing nucleic acid is radiolabeled.

4. The method of any of claims 1, 2 or 3 wherein said ribosomal RNA information-containing nucleic acid probe is ribosomal RNA.

5. The method of any of claims 1, 2 or 3 wherein said ribosomal RNA information-containing nucleic acid probe is DNA complementary to ribosomal RNA.

6. The method of claims 1, 2 or 3 wherein said ribosomal RNA information-containing nucleic acid probe is DNA obtained by nick-translating or cloning DNA complementary to ribosomal RNA.

7. The method of claim 1 wherein said unknown organism being characterized is a cell or cells of a strain in an in vitro culture.

8. The method of claim 1 wherein said unknown organism being characterized and said probe organism are both from the same taxonomic group selected from the group consisting of a kingdom, subkingdom, division, subdivision, phylum, subphylum, class, subclass, order, family, tribe and genus.

9. The method of claim 1 wherein said unknown organism being characterized and said probe organism are both eukaryotic.

10. The method of claim 1 wherein said unknown organism being characterized and said probe organism are both prokaryotic.

11. The method of claim 1 wherein said unknown organism being characterized is eukaryotic and said probe organism is prokaryotic.

12. The method of claim 1 wherein said unknown organism being characterized is prokaryotic and said probe organism is eukaryotic.

13. The method of any of claims 10 or 12 wherein said unknown prokaryotic organism being characterized is selectively being detected while present in or associated with a eukaryotic organism.

14. The method of claim 13 wherein said unknown prokaryotic organism is a bacterium.

15. The method of claim 13 which comprises:
    extracting the total DNA of said prokaryotic and said eukaryotic organisms, and
    selectively detecting the ribosomal RNA information present in the DNA of said prokaryotic organism, in the presence of ribosomal RNA information present in the DNA of said eukaryotic organism.

16. The method of claim 9 wherein the DNA from said unknown eukaryotic organism being characterized is nuclear DNA and the ribosomal RNA information-containing nucleic acid from said eukaryotic probe organism not derived from mitochondria or chloroplasts.

17. The method of claim 9 wherein the DNA from said unknown eukaryotic organism being characterized is mitochondrial DNA and the ribosomal RNA information-containing nucleic acid from said eukaryotic probe organism is derived from mitochondria or chloroplasts.

18. The method of claim 9 wherein DNA from said unknown eukaryotic organism being characterized is chloroplast DNA and the ribosomal RNA information-containing nucleic acid from said eukaryotic probe organism is derived from mitochondria or chloroplasts.

19. The method of claim 11 wherein said DNA from said unknown eukaryotic organism being characterized is derived from mitochondrial DNA.

20. The method of claim 11 wherein said DNA from said unknown eukaryotic organism being characterized is derived from chloroplast DNA.

21. The method of claim 12 wherein said ribosomal RNA information containing-nucleic acid probe is derived from mitochondria or from chloroplasts.

22. The method of any of claims 9 or 11 which further comprises identifying in said unknown eukaryotic organism being characterized a nucleic acid sequence or sequences creating a taxon below the rank of species or an infrasubspecific subdivision.

23. The method of claim 22 wherein said nucleic acid sequence or sequences comprises a virus and virus-derived DNA.

24. A method of establishing the species of an unknown bacterial strain present in a sample, which comprises:
    (1) providing a chromatographic pattern representing the hybridization of ribosomal RNA information-containing nucleic acid from or derived from a known probe bacterium to restriction endonuclease-digested DNA from an unknown bacterial
    (2) comparing said pattern with a number of additional chromatographic patterns sufficient to enable the establishment of such species; each one of said additional chromatographic patterns representing the hybridization of ribosomal RNA information-containing nucleic acid from or derived from a known probe bacterium, to restriction endonuclease-digested DNA from a known different bacterial species; and (3) establishing the species of said unknown bacterial strain by means of a set of ribosomal RNA sequence-containing restriction fragments present in said chromatographic pattern of said unknown bacterial strain; said set being conserved among different strains of said species, but not conserved among different species.

25. The method of claim 24 wherein said unknown bacterium is present in a fermentation medium or in a secretion or excretion product.

26. The method of claim 24 wherein said chromatographic patterns of known bacteria are present in a catalog containing patterns for at least two different bacteria.

27. The method of claim 24 wherein said unknown bacterium is present in or associated with eukaryotic tissue.

28. The method of claim 27 wherein said bacterium is present in or associated with animal or plant cells.

29. The method of claim 28 wherein said bacterium is present in or associated with human cells, or associated with plant root cells.

30. The method of claim 27 which comprises:
extracting the total DNA of said bacterium and said eukaryotic tissue, and
selectively detecting the ribosomal RNA information present in the DNA of said bacterium, in the presence of ribosomal RNA information present in the DNA of said eukaryotic tissue.

31. The method of claim 24 which further comprises detecting in said bacterial strain for the presence of a nucleic acid sequence or sequences creating a taxon below the rank of species, or an infrasubspecific subdivision.

32. The method of claim 31 wherein said nucleic acid sequence or sequences are all or part of a bacteriophage genome.

33. The method of claim 31 wherein said nucleic acid sequence or sequences are all or part of an extrachromosomal genetic element, a plasmid, or an episome.

34. The method of claim 31 wherein said sequence or sequences code for an R-factor or for an antibiotic resistance factor.

35. The method of any of claims 24, 25, 27, or 29 wherein said unknown bacterium is pathogenic towards plants or animals.

36. The method of any of claims 24, 25, 27, or 29 wherein said ribosomal RNA information-containing nucleic acid from or derived from said probe bacterium is detectably labeled.

37. The method of claim 36 wherein said label is a radiolabel.

38. The method of claim 36 wherein said nucleic acid from or derived from said probe bacterium is ribosomal RNA.

39. The method of claim 36 wherein said nucleic acrid from or derived from said probe bacterium is complementary DNA to ribosomal RNA.

40. The method of any of claims 1 or 24 wherein said ribosomal RNA sequence containing nucleic acid is part of a plasmid.

41. The method of any of claims 1 or 24 wherein several chromatographic patterns of restriction endonuclease digested DNA from said unknown organism are prepared, each of said several patterns corresponding to a different restriction endonuclease enzyme.

* * * * *